(12) United States Patent
Yadidi

(10) Patent No.: US 10,813,881 B2
(45) Date of Patent: Oct. 27, 2020

(54) DRY POWDER INHALATION DEVICE

(71) Applicant: OTITOPIC INC., Los Angeles, CA (US)

(72) Inventor: Kambiz Yadidi, Los Angeles, CA (US)

(73) Assignee: OTITOPIC INC., Los Angeles, CA (US)

( * ) Notice: Subject to any disclaimer, the term of this patent is extended or adjusted under 35 U.S.C. 154(b) by 339 days.

(21) Appl. No.: 15/703,934

(22) Filed: Sep. 13, 2017

(65) Prior Publication Data

US 2018/0311156 A1   Nov. 1, 2018

Related U.S. Application Data

(60) Provisional application No. 62/491,640, filed on Apr. 28, 2017.

(51) Int. Cl.
*A61K 9/00* (2006.01)
*A61M 15/00* (2006.01)
*A61M 11/00* (2006.01)

(52) U.S. Cl.
CPC ......... *A61K 9/0075* (2013.01); *A61M 15/003* (2014.02); *A61M 15/0045* (2013.01); *A61M 11/003* (2014.02); *A61M 15/002* (2014.02); *A61M 15/0008* (2014.02); *A61M 15/0021* (2014.02); *A61M 15/0068* (2014.02); *A61M 15/0096* (2014.02); *A61M 2202/064* (2013.01); *A61M 2205/43* (2013.01)

(58) Field of Classification Search
CPC ............ A61K 9/0075; A61M 15/0045; A61M 15/003; A61M 2205/43; A61M 15/0096; A61M 11/003; A61M 15/002; A61M 15/0021; A61M 15/0068; A61M 2202/064; A61M 15/0008
See application file for complete search history.

(56) References Cited

U.S. PATENT DOCUMENTS

| | | | | |
|---|---|---|---|---|
| 3,971,377 A | * | 7/1976 | Damani | A61M 15/0028 128/200.17 |
| 4,739,754 A | * | 4/1988 | Shaner | A61M 15/0008 128/203.12 |
| 5,727,546 A | * | 3/1998 | Clarke | A61M 15/0028 128/203.15 |

FOREIGN PATENT DOCUMENTS

WO   WO-2017079397 A1 *  5/2017  ............... A61K 9/00

* cited by examiner

*Primary Examiner* — Timothy A Stanis
*Assistant Examiner* — Arielle Wolff
(74) *Attorney, Agent, or Firm* — FisherBroyles, LLP; James W. Hill

(57) ABSTRACT

Delivery of a dry powder via inhalation can be performed using an inhalation device having an inhalation tube and a hollow extension housing an assembly of components including a plurality of impellers, a puncturing device, and a dry powder container. The delivery of dry powder through the inhalation device is facilitated by the puncturing device puncturing the dry powder container, the impellers directing air flow, and the configuration of the extension and inhalation tube.

17 Claims, 38 Drawing Sheets

DRY POWDER INHALATION DEVICE

CROSS-REFERENCE TO RELATED APPLICATIONS

This application claims the priority benefit of U.S. Provisional Patent Application No. 62/491,640, filed Apr. 28, 2017, and incorporated herein by reference in its entirety.

BACKGROUND

Pulmonary delivery of therapeutic agents offers several advantages over other modes of delivery. These advantages include rapid onset of action, convenience of patient self-administration, a potential for reduced drug side effects, ease of delivery by inhalation, and elimination of needles. Inhalation therapy is capable of being easy to use in an inpatient or outpatient setting, results in very rapid onset of drug action, and produces minimal side effects. In addition, dry powder inhalation offers the possibility of delivering accurate and reproducible doses of a drug to the pulmonary vasculature.

SUMMARY OF THE INVENTION

A dry powder inhalation device is provided. In certain embodiments, the dry powder inhalation device comprises:
a. an inhaler body, the inhaler body comprising one or more sidewalls extending between an open first end and an open second end and surrounding an interior volume, at least a portion of the inhaler body being sized and shaped to receive an assembly of components within the interior volume; and
b. the assembly of components, wherein the components are arranged in series within the interior volume and include:
  i. a dry powder container that contains a measured amount of dry powder, wherein one or more walls of the dry powder container are configured to be selectively opened thereby allowing the dry powder to be released from the container into the internal volume of the inhaler body, and
  ii. a plurality of impellers positioned within the internal volume, wherein each of the a plurality of impellers has a top side and an opposing bottom side and includes a series of blades defining openings therebetween and is configured to rotate about a respective central axis, and wherein the a plurality of impellers are configured to direct air and the released dry powder toward the first end.

These and other aspects, features, and advantages can be appreciated from the accompanying description of certain embodiments of the invention and the accompanying drawing figures and claims.

BRIEF DESCRIPTION OF THE DRAWINGS

The present invention is illustrated by way of example, and not limitation, in the figures of the accompanying drawings, in which.

DETAILED DESCRIPTION

Disclosed herein is a device for the delivery of a dry powdered or aerosolized substance (typically a medication) to a user via inhalation. In some embodiments, delivery of the dry powdered or aerosolized substance may be enabled by an inhalation device configured such that a user inhaling a breath from an end of the inhalation device (e.g., placing their mouth over the end and drawing air through the inhalation device) creates a negative pressure on a capsule containing the dry powdered substance thereby drawing the dry powdered substance from the capsule into the mouth and/or lungs of the user via the dry powder inhalation device (also referred to as the inhalation device or inhaler device).

In one embodiment, the inhalation device disclosed herein may be used to deliver dry powdered or aerosolized respirable dry powders that comprise, for example and without limitation, an NSAID, such as acetylsalicylic acid, as the active ingredient. The respirable dry particles may vary in size, e.g., a geometric diameter (VMGD) between 0.5 μm and 30 μm. Alternatively, the respirable dry powders can have a mass median aerodynamic diameter (MMAD) of about 20 μm or less. Optionally, the MMAD of the particles may be between 0.5 and 10 μm or between 1 and 10 μm. Exemplary dry powder compositions that can be administered using a dry powder inhalation device in accordance with the disclosed embodiments are further described in U.S. Provisional Application Ser. No. 62/251,240, titled DRY POWDER INHALATION DEVICE and filed on Nov. 5, 2015, which is hereby incorporated by reference as if disclosed in its entirety herein.

Figure 1A:
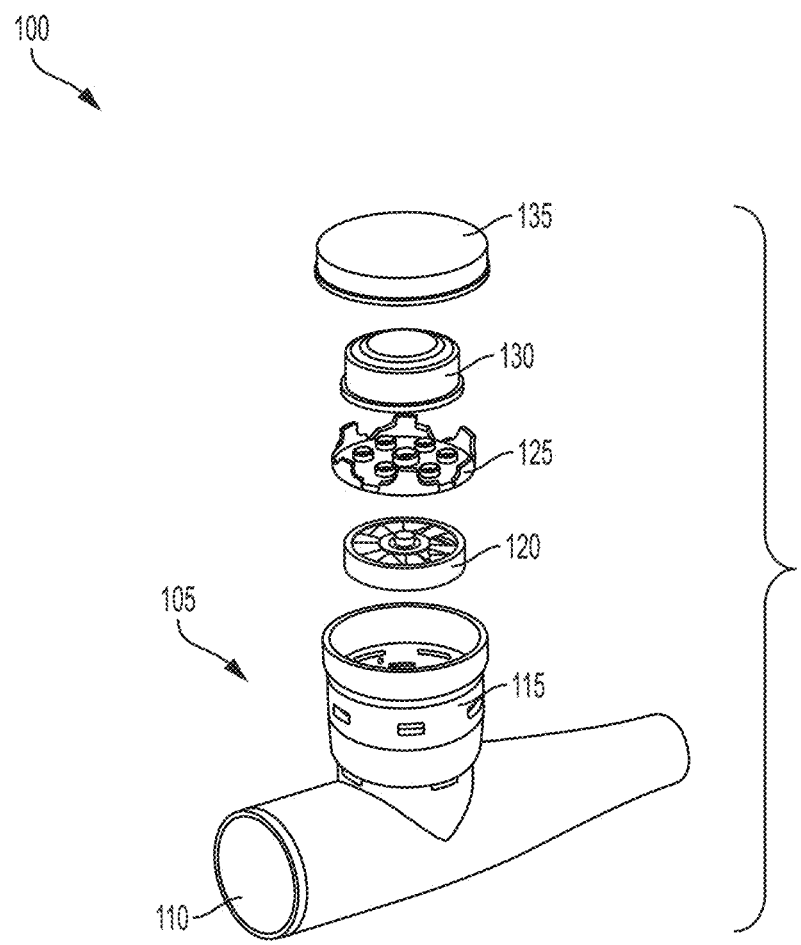
FIG. 1A depicts an exploded top perspective view of an exemplary dry powder inhaler in accordance with some embodiments of the present invention.
Figure 1B:
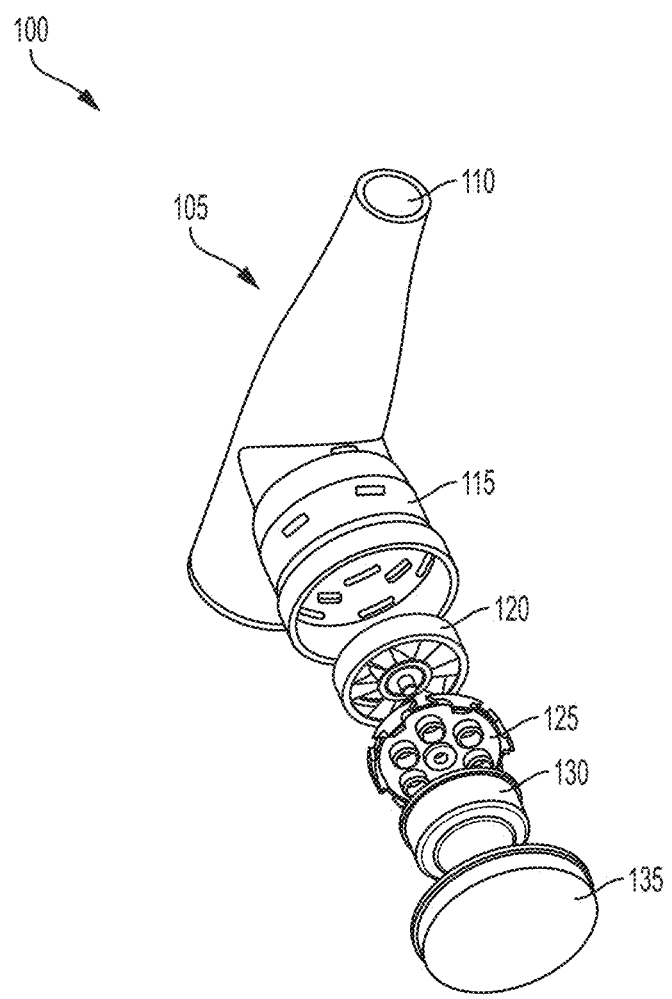
FIG. 1B depicts an exploded view of the exemplary dry powder inhaler of FIG. 1 in accordance with some embodiments of the present invention.

FIGS. 1A and 1B depict exploded views from various perspectives of an exemplary dry powder inhaler 100 for use with a dry powder in accordance with one or more of the exemplary embodiments. More specifically, FIG. 1A illustrates an exploded view of an exemplary dry powder inhaler 100 from a top to bottom perspective and FIG. 1B illustrates an exploded view of an exemplary dry powder inhaler 100 from a bottom to top perspective.

Figure 1C:
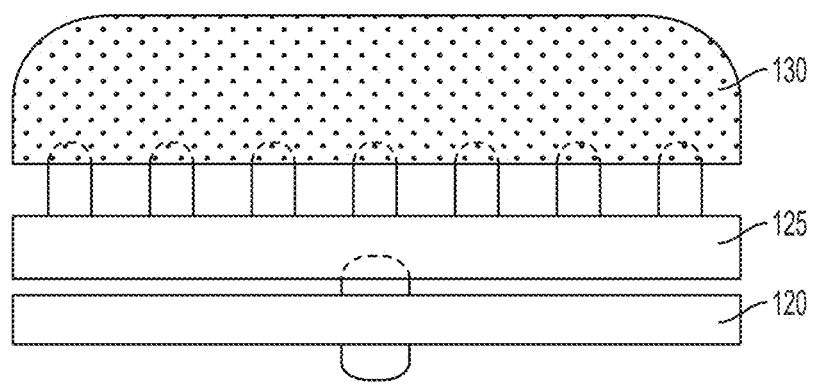
FIG. 1C depicts an assembled view of components of the exemplary dry powder inhaler of FIG. 1 in accordance with some embodiments of the present invention.
Figure 1D:
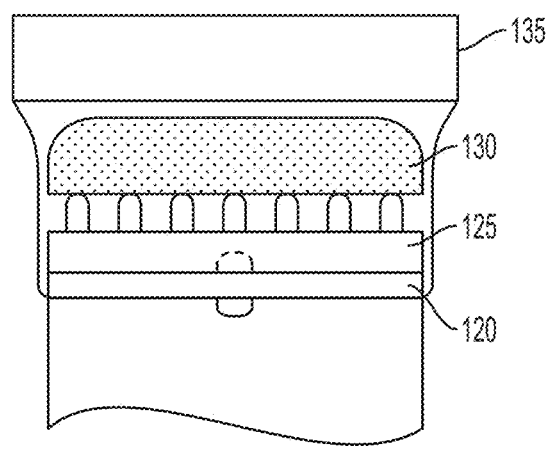
FIG. 1D depicts a cut-away view of assembled components of the exemplary dry powder inhaler of FIG. 1 in accordance with some embodiments of the present invention.

As shown, the dry powder inhaler 100 includes an inhaler body 105 with an inhalation tube 110 and an extension 115. Extension 115 is sized and positioned to extend from an outer surface of the inhalation tube 110 such that an assembly of an impeller 120, a puncturing device 125, and a dry powder container 130 can be positioned therein. In addition, a cap 135 may be positioned on top of the extension 115 so as to, for example, secure the assembly of the impeller 120, the puncturing device 125, and the dry powder container 130 within the extension 115. In one embodiment, all of the components of the assembly (i.e., the impeller 120, the puncturing device 125, and the dry powder container 130) can be circular in shape and sized so as to fit together with one another and within the extension 115. FIG. 1C depicts a side view of the components (impeller 120, puncturing device 125 and dry powder container 130) in an assembled state and FIG. 1D depicts a cut-away view of the assembly disposed within the extension 115, in accordance with some embodiments of the present invention.

Exemplary dimensions for the components of dry powder inhaler 100 are as follows:
 inhalation tube 110: 70-76 mm in length
 extension 115: 18-21 mm in length
 impeller 120: 16-18 mm in diameter
 puncturing device 125: 16-18 mm in diameter
 dry powder container 130: 16-18 mm in diameter It will be appreciated by those of skill in the art that the shapes of the dry powder inhaler 100 and/or the components thereof (e.g., inhaler body 105, inhalation tube 110, extension 115, impeller 120, puncturing device 125, and/or dry powder container 130) may be any appropriate shape or size. For example, the shape of dry powder inhaler 100 and/or the components thereof may be circular, oval, square, triangular, octagonal, or rectangular in shape or may be a combination of shapes. For instance, an inhalation tube 110 having a square cross-section can be provided along with a circular extension 115 that is sized and shaped to accommodate a circular impeller 120, an octagonal puncturing device 125, and a square dry powder container 130 therein.

Figure 2A:
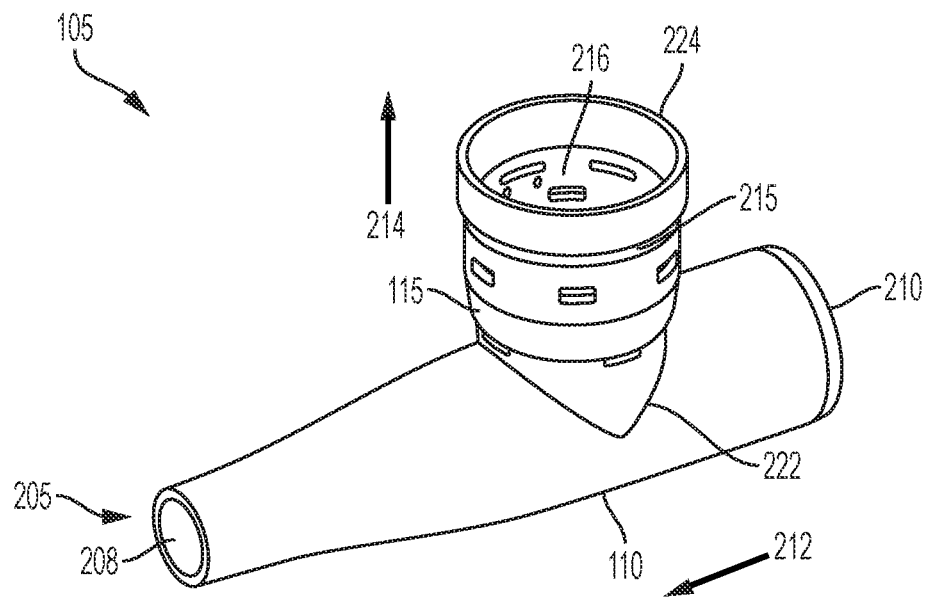
FIG. 2A provides a top-perspective views of an inhaler body of the inhaler of FIG. 1 in accordance with some embodiments of the present invention.
Figure 2B:
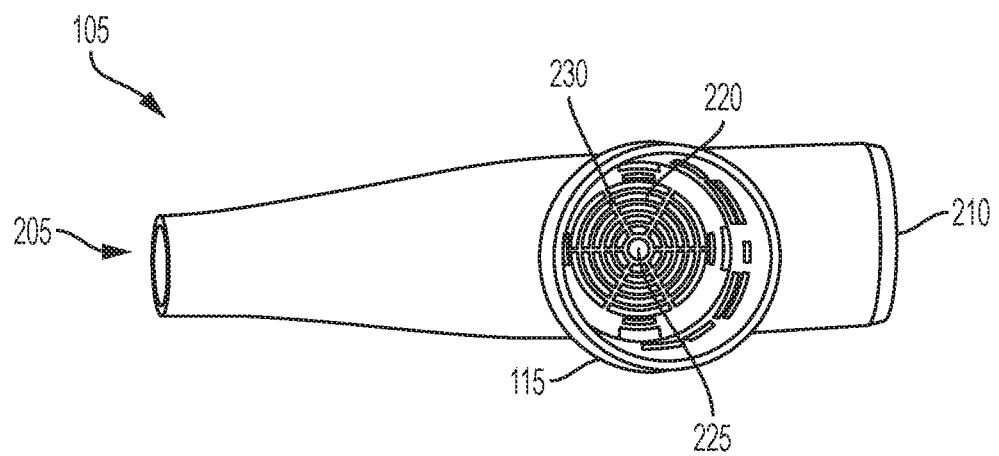
FIG. 2B provides a top view of the inhaler body of FIG. 2A in accordance with some embodiments of the present invention.
Figure 2C:
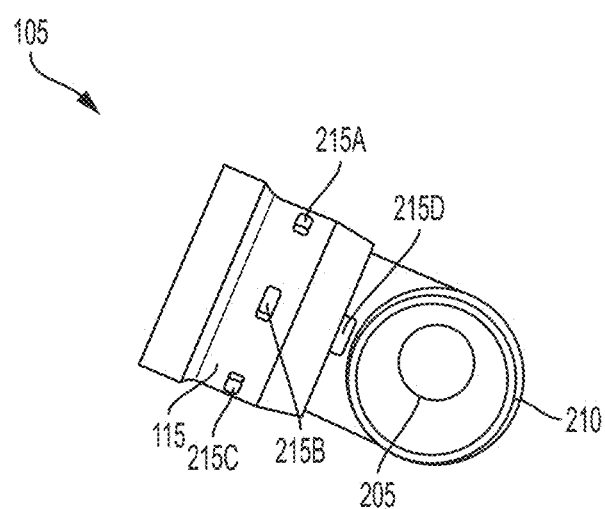
FIG. 2C provides a back-view of the inhaler body of FIG. 2A in accordance with some embodiments of the present invention.

FIGS. 2A-2C provide various views of the exemplary inhaler body 105. More specifically, FIG. 2A is a top perspective view of the inhaler body 105 showing that a first end 205 of inhalation tube 110 that has a smaller interior diameter than a second end 210 of inhalation tube 110, which has a larger interior diameter than the first end 205. The sidewalls defining the tube-shaped inhalation tube 110 surround an interior volume 208. The diameter and relative size of the two open ends of the inhalation tube 110 and generally hollow configuration can be sized and shaped to facilitate the flow of air and dry powder through the interior volume of the inhalation tube when a user draws a breath from the first end 205. As shown, the inhalation tube is generally tube-shaped and extends primarily in a horizontal direction 212.

The extension 115 can be a generally hollow structure that extends from an outer side or surface of the inhalation body. For instance, the extension 115 can comprise one or more sidewalls that extend in a vertical direction 214 between a first end 222 that is located at a top side of the inhalation tube 110 and an open second end 224. In addition, the walls of the extension surround a generally open interior space or volume 216. In some instances, the extension can be at least partially defined by a portion of the inhalation body 105 that extends away from the main lengthwise oriented portion of the inhalation body 105. Accordingly, the extension can be comprised of a single continuous structure or one or more individual components that are fixedly or removably joined to define the extension 115.

Preferably, the extension 115 is sized and configured so as to accept the assembly of the impeller 120, the puncturing device 125, and the dry powder container 130 within the interior volume of the extension thereby housing at least a portion of the assembly. In some cases, the extension 115 may include one or more locating features, such as notches, protrusions or other mechanical mechanisms for accommodating insertion, placement and/or retention of a component of the assembly of the impeller 120, the puncturing device 125, and the dry powder container 130 in the extension 115. Accordingly, the components of the assembly can also include one or more locating features that are provided on an outer surface of the component and that have a complementary shape so as to matingly engage with the locating features provided at the interior surface of the extension 115. For instance, the locating feature can be a protrusion from the interior wall of the extension that is sized and shaped to engage a complementary notch that is provided in an outer edge of the puncturing device so as to retain the puncturing device at a suitable level and orientation within the interior of the extension. By way of further example, the locating feature can be a ridge that extends around the interior surface of the extension at a given level and that has a smaller diameter than the dry powder container so as to prevent the dry powder container from being inserted too deep within the extension.

The cap 135 may be sized so as to fit on top of the extension 115 and thereby can secure the assembly of the impeller 120, the puncturing device 125, and the dry powder container 130 within the extension 115 during use and/or storage. In addition, as further described herein, the cap can also be configured to facilitate the use of the inhalation device.

In some embodiments, the sidewall of extension 115 can include one or more openings 215 that extend through the thickness of the sidewall. The openings 215 can serve to facilitate air flow through the dry powder inhalation device 100 and, in some instances, may act as windows so that a user may visually confirm the placement of one or more dry powder inhalation device 100 components positioned therein. More specifically, the one or more openings 215 facilitate air flow from outside of the extension into the interior volume of the extension.

The openings can be located at various levels within the extension so as to facilitate the flow of air through one or more components of the assembly. For instance, as shown in FIG. 2C, preferably, one or more lower side openings 215D are provided through the side wall of the extension at a level that is above the bottom-most first end of the extension (in the vertical direction 214). The lower side opening 215D can also be provided at a level that is below one or more components of the assembly housed within the extension 115, for instance, the impeller (not shown). Accordingly, in the inflow of air through lower side opening 215D from below the impeller can facilitate the flow of air and dry powder from the interior volume of the extension into the interior volume of the inhalation tube as further described herein. Similarly, as shown in FIG. 2C, upper side openings 215A-C, can be provided at a level that is above one or more of the assembly components housed within the extension 115. For instance, the upper side openings 215A-C can be provided at a level that is above the impeller (not shown) and that is below the bottom lid of the dry powder container when assembled for use. Accordingly, in the inflow of air through upper side openings 215A-C can facilitate the evacuation of dry powder from the dry powder container and can facilitate the flow of air and/or dry powder through the impeller toward the interior volume of the inhalation tube, as further described herein.

FIG. 2B provides a top plan view of the inhaler body 105 and depicts a bottom structure or "wall" of the extension 115. In this exemplary implementation, the bottom includes a grid 220 of openings therethrough and is configured to allow passage of air as well as a dry powder therethrough. Although the bottom including the grid 220 are described as being a part of the extension 115, the bottom can similarly be defined by a portion of the inhalation tube that is bounded by the extension 115. For instance, a portion of the top wall of the inhalation tube 110 can be cut to define the grid openings and the extension 115 can be provided around the so defined grid 220. Similarly, in the case where the extension 115 is at least partially defined by a vertically oriented extension of the inhalation tube 110, the bottom can be provided across such an extension. Moreover, although the structure including the grid 220 is described as being a "bottom" structure or wall of the extension, the structure need not be located at the bottom-most first end 222 of the extension 115. For instance, the structure including the grid 220 can be disposed at a level within the interior volume of the extension that is set above the first end in the vertical direction 214.

As shown in FIG. 2B, the bottom of extension 115 can also have a center opening 225 into which an axis pin of impeller 120 may be inserted. Grid 220 may include a plurality of openings of any appropriate size that may be arranged in any appropriate manner. For example, in FIG. 2B, grid 220 comprises a series of semi-circular openings concentrically radiating outwardly from center opening 225 with six solid support structures 230 extending outwardly from the center opening 225 toward the interior surface of extension 115. In other embodiments, grid 220 may comprise a mesh structure provided at or near the bottom end of the extension 115 so as to prevent particles of dry powder and/or a portion of dry powder container 130 having a diameter greater than the mesh from passing through the mesh and entering the interior volume 218 of the inhalation tube 110. In some embodiments, the bottom wall can comprise one or more support structures and one or more openings that allow passage of air and dry powder from the interior of the extension into the interior of the inhalation tube. In addition or alternatively embodiments, a bottom structure can be omitted so as to provide an unobstructed opening allowing air and/or dry powder to pass more freely between the interior volume of the extension 216 and the interior volume of the inhalation tube 218.

FIG. 2C provides a side plan view of the second side of inhaler body 105, which shows the relative diameter of the first end of inhalation tube 205 compared to the larger diameter of the second end of inhalation tube 210. The difference in diameter between the first and second end, as well as the cross-sectional profile the inhalation tube extending between the two ends can be varied so as to improve the flow of air when a negative pressure is applied to the first end.

Figure 3A:
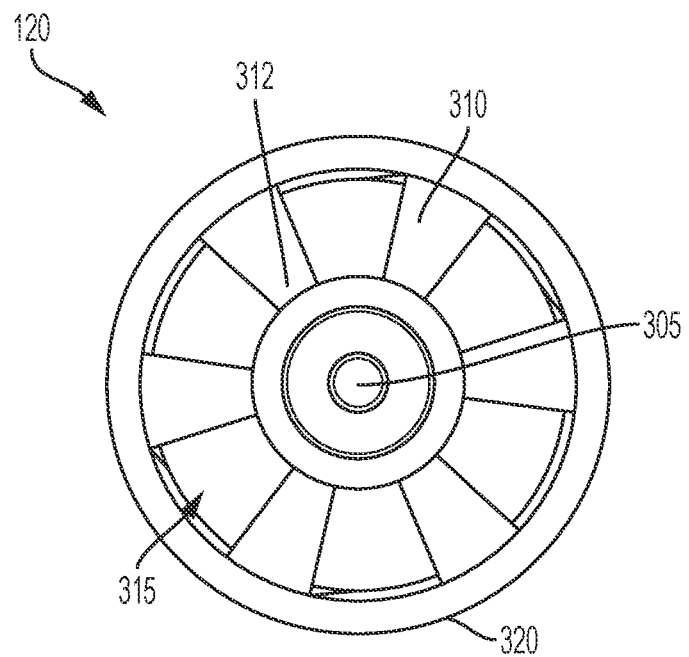
FIG. 3A provides a top view of an impeller in accordance with some embodiments of the present invention.
Figure 3B:
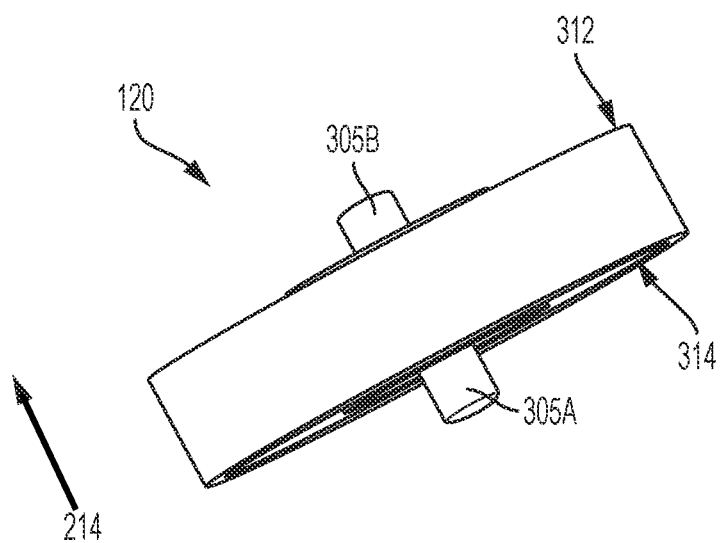
FIG. 3B provides a side view of an impeller in accordance with some embodiments of the present invention.
Figure 3C:
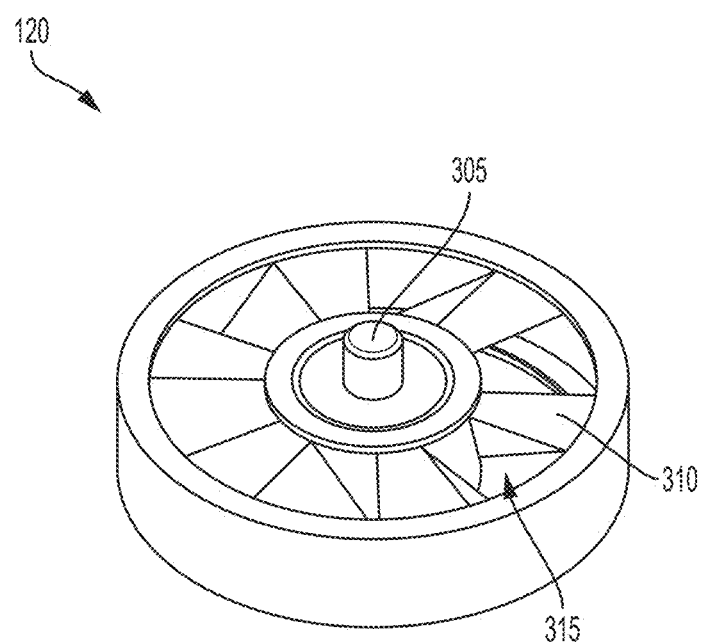
FIG. 3C provides a perspective view of the impeller of FIG. 3A in accordance with some embodiments of the present invention.

FIGS. 3A-3C depict various views of an exemplary impeller 120 in accordance with one or more of the disclosed embodiments. FIG. 3A provides a top plan view of impeller 120, FIG. 3B shows a side view of impeller 120, and FIG. 3C shows a side perspective view of impeller 120.

As can be seen in FIGS. 3A-3C, the exemplary impeller 120 can include an axis pin 305, multiple blades 310, multiple openings 315 between the blades and an outer edge 320. The impeller also has a top side 312 and a bottom side 314. Preferably, for use, the impeller is disposed within the interior volume of the extension 115 such that the bottom side 314 of the impeller is facing downwards in the vertical direction 214 (e.g., toward the interior volume of the inhalation tube 218).

Figure 4A:
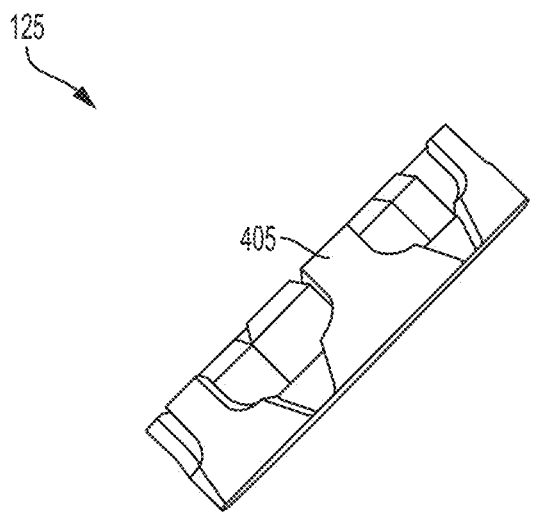
FIG. 4A provides a side view of a puncturing device in accordance with some embodiments of the present invention.
Figure 4B:
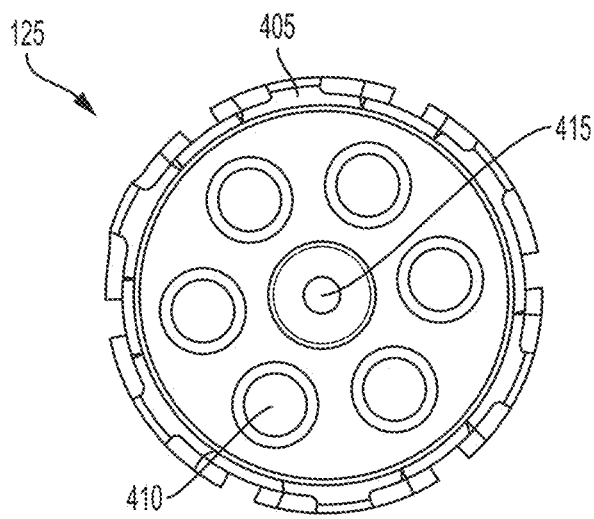
FIG. 4B provides a top view of the puncturing device of FIG. 4A in accordance with some embodiments of the present invention.
Figure 4C:
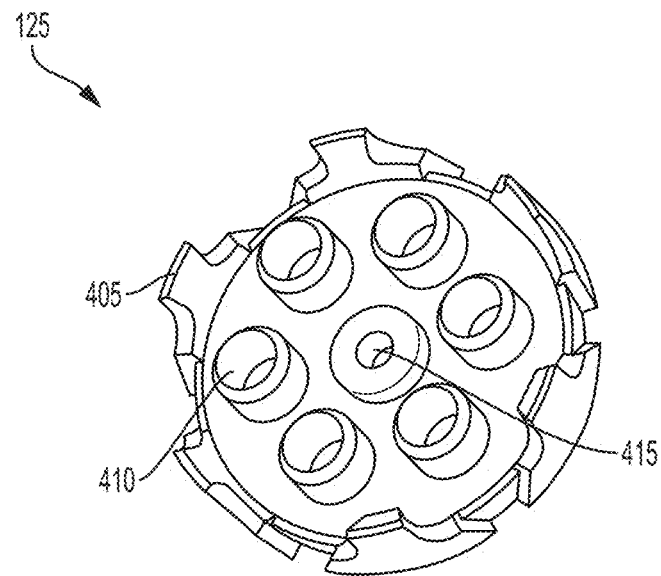
FIG. 4C provides a top perspective view of the puncturing device of FIG. 4A in accordance with some embodiments of the present invention.
Figure 4D:
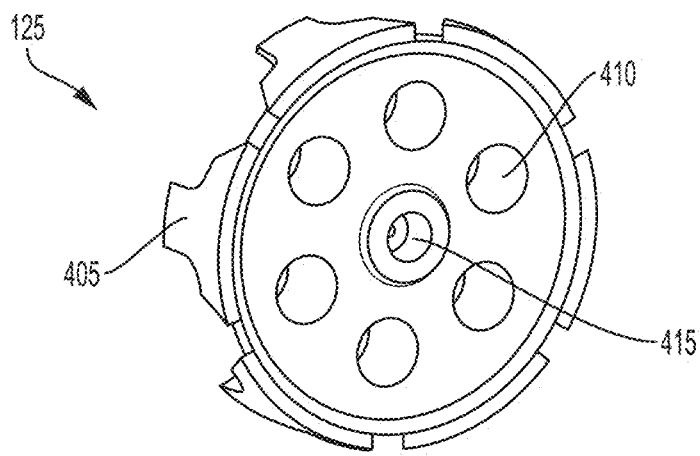
FIG. 4D provides a bottom perspective view of the puncturing device of FIG. 4A in accordance with some embodiments of the present invention.

In some embodiments the axis pin 305 can extend along the central axis of rotation of the impeller. For instance, as shown in FIG. 3B, a bottom axis pin 305A can extend from the bottom side of the impeller. The bottom end of the axis pin 305A can be sized and shaped to correspond with a complementary mount that is provided within the extension 115. For instance, as shown in FIG. 2B, the mount can be a center opening 225 that is formed in the center of the bottom wall of the extension 115 so as to receive the bottom axis pin 305A therein. Accordingly, the impeller can freely rotate in a circular/rotational direction about the axis pin. In some implementations, the axis pin can be configured to rotate within the mount. In another exemplary configuration the axis pin can extend through the center of the impeller and the impeller can be configured to rotate about the central axis pin, for instance, using bearing assembly sealed within the impeller and surrounding the central axis pin. As shown in FIG. 3B, the impeller 120 can also include a top axis pin 305B that extends from the top side 312 of the impeller. In such a configuration, the top end of axis pin 305B can be received by a corresponding mount that is provided above the top side of the impeller and that retains the impeller in position from above. For instance, a mount or center opening (e.g., 415 of FIG. 4B) can be formed in the center of the bottom side of the puncturing device 120 and configured to receive the top end of axis pin 305A therein similar to the exemplary bottom mount.

Alternative mounting configurations can be implemented to support the impeller so as to allow the impeller to rotate without departing from the scope of the disclosed embodiments. For instance, in another exemplary configuration, the impeller can be supported within an impeller housing (not shown) such that the impeller can rotate freely within the housing. In such an exemplary configuration, the housing can include one or more mounts provided near the central axis of the impeller, as described previously. In addition or alternatively, the impeller can be rotatably supported at or near its outer edge 320, for instance by one or more bearing assemblies supporting the impeller from below and/or above the outer edge of the impeller. Preferably, in such a configuration, the impeller housing can include openings in both a top and bottom end of the housing allowing air and/or dry powder to pass of the housing and the impeller.

Impeller 120 may have a number of blades 310 (e.g., 6, 8, 10, etc.) provided in a variety of different patterns. Each blade can be adjacent to a corresponding opening 315. The impeller and the blades can be positioned such that, when a user applies a negative pressure to the first end of the inhalation body 105 (for example, by the user inhaling through the first end 205) and draws air through the inhalation tube, a force is applied to the impeller 120 causing the impeller to rotates about a central axis. Accordingly, blade 310 may further act to move air and/or dry powder through openings 315 and direct the air and/or dry powder toward the interior volume of the inhalation tube. In some embodiments, the impeller 120 aerosolizes the dry powder to facilitate the evacuation of the dry powder from the dry powder container 130 and further directs it through the inhalation tube 110 toward the first end 105. It should be understood that a variety of impeller and/or propeller designs can be implemented to assist the flow of air and dry powder through the interior volume of the inhalation device during use without departing from the scope of the exemplary embodiments.

FIGS. 4A-4D show various views of puncturing device 125. In the exemplary configuration shown, puncturing device 125 can be circular in shape and can include a plurality of blades 405 and/or circular extensions 410 and a center opening 415.

As previously noted, center opening 415 of the puncturing device 125 can be configured to receive the top end of the impeller axis pin therein thereby maintaining the impeller in position and allowing the impeller to rotate about its central axis. When inserted into extension 115 after impeller 120, center opening 415 may be sized and positioned so as to correspond to axis pin 305 of impeller 120 so that axis pin 305 may be inserted into center opening 415.

Puncturing device 125 can have any number of extensions 410 (e.g., 1-100) that extend from a top side of the puncturing device toward a free end. These extensions can be located on the top side in any arrangement, such as a random pattern, a radial pattern or a grid-like pattern. The free end of the extensions 410 can include a sharp edge or blade-like edge that may serve to puncture a bottom lid of the dry powder container 130, which will be discussed below with regard to FIGS. 5A and 5B. In some instances, extensions 410 may be cut, or otherwise manufactured, so that the upper edge (i.e., the edge that comes into contact with the bottom lid of the dry powder container) is at an angle (e.g., 30°, 45°, 60°, etc.) relative to the bottom end of puncturing device 125 so as to facilitate puncturing of the bottom lid 510 of the dry powder container. The extensions 410 may be of any length including, but not limited to, 3 mm, 5 mm, 7 mm, 10 mm, etc. In addition, the inner diameter of the extensions 410 can be, for example, 0.8 mm-1.5 mm.

In some embodiments, extensions 410 may be cylindrical in shape and may be hollow in the center so that dry powder and/or air may flow through the hollow center of the extensions 410 through the puncturing device. In some instances, extensions 410 may be of, for example, square, triangular, rectangular, and/or oval shaped.

Figure 5A:
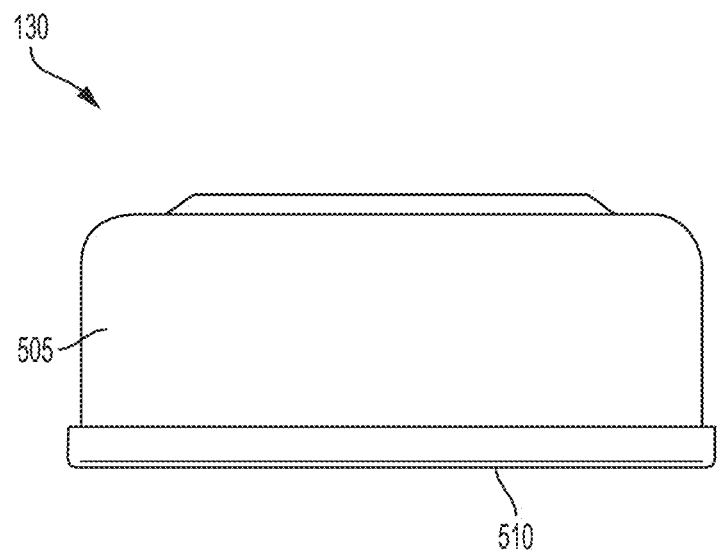
FIG. 5A provides a side view of a dry powder container in accordance with some embodiments of the present invention.
Figure 5B:
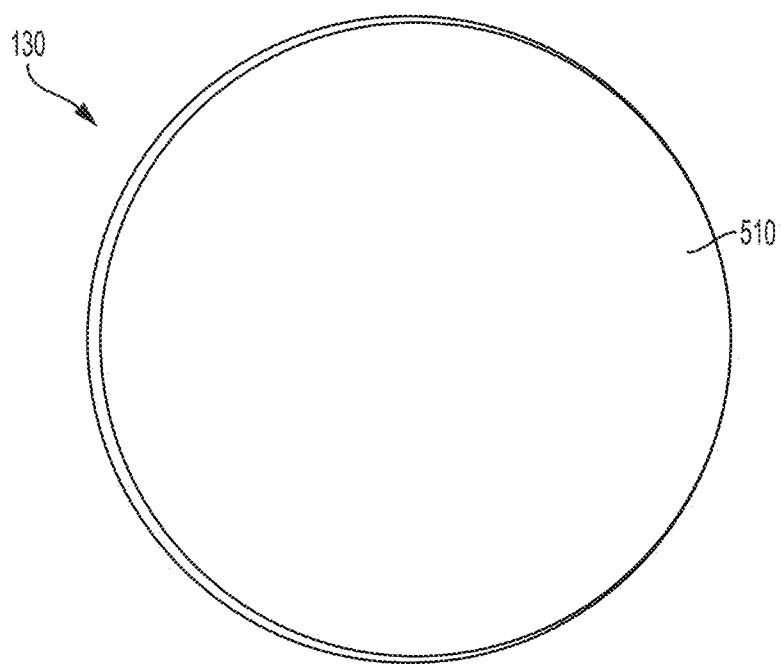
FIG. 5B provides a bottom view of the dry powder container of FIG. 5A in accordance with some embodiments of the present invention.

FIG. 5A is a side plan view of dry powder container 130 and FIG. 5B is a top view of dry powder container 130. Dry powder container 130 may include a cup portion 505 and a lid, or cover 510. Cup portion 505 may be shaped so as to contain, or hold, a desired amount (e.g., mass or volume) of dry powder and have an open bottom end. Cup portion 505 may be made from a relatively rigid material like a stiff foil or plastic. Lid 510 may be configured, sized, and positioned so as to seal the open end of cup portion. Lid 510 may be made from a material that can be punctured by one or more of the extensions 410 when the extension 410 is pushed through the lid 510. Lid 510 may be made from any appropriate material including, but not limited to, a foil, a bio-compatible material, bio-absorbable gel, a plastic, etc. Preferably, lid 510 will be comprised of a suitable material such that extensions 410 may puncture lid 510 and dry powder may be expelled from dry powder canister 130.

Dry powder container 130 may contain, for example, an appropriate mass (e.g., 5 mg-150 mg) of a dry powder or medicine. The dry powder may be compacted into dry powder container 130 with any appropriate density based on, for example, dosage amount and/or characteristics of the dry powder or medicine to be delivered. In some circumstances, dry powder container 130 may include a propellant or other mechanism for assisting with the expelling of the dry powder from dry powder container 130 when dry powder container 130 is punctured by puncturing device 125. In some embodiments, dry powder container 130 may be filled, for example, 50-90% by volume.

Additionally, or alternatively, dry powder container 130 may be vacuum packed such that the interior portion of dry powder container is under a vacuum with reference to the exterior air. In this circumstance, when dry powder container 130 is punctured, for example by puncturing device 125, breaking the vacuum seal may serve to expel dry powder from the dry powder container 130. By way of further example, in some exemplary implementations, the dry powder container can be made of a flexible material and sized and shaped such that insertion of the dry powder container into the extension and/or placement of the cap over the end of the extension can increase the interior pressure of the dry powder container. Accordingly, the additional pressure within the dry powder container can serve to expel the dry powder from the container when the bottom lid is punctured by the puncturing device.

Figure 6A:
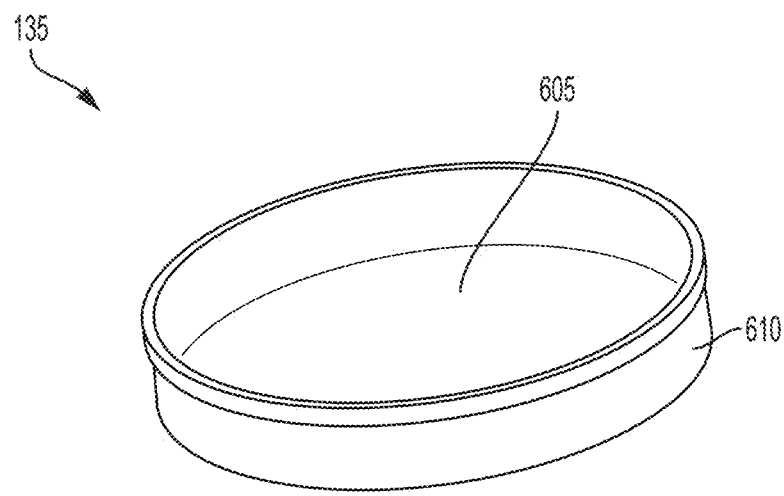
FIG. 6A provides a perspective view of a cap in accordance with some embodiments of the present invention.
Figure 6B:
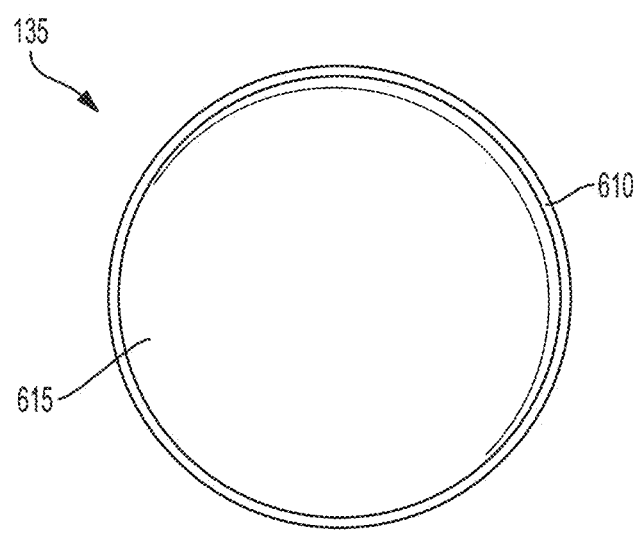
FIG. 6B provides a bottom view of the cap of FIG. 6A in accordance with some embodiments of the present invention.

FIG. 6A depicts an interior side perspective view of cap 135 and FIG. 6B provides a top plan view of cap 135. Cap 135 may be sized so as to securely fit on top of extension 115. Cap 135 may include an indented area 605 configured to fit over extension 115 and to accommodate positioning of a portion of capsule 130 therein. Cap 135 may also include a sidewall 610 sized and shaped so as to fit over an end of extension 115.

In some circumstances, when cap 135 is placed over the assembly of the impeller 120, puncturing device 125, and dry powder capsule 130 and pushed down so as to fit on top of, or otherwise engage with, extension 115, the downward pressure on cap 135 may be transferred to one or more of dry powder capsule 130 and puncturing device 125 so as to push extensions 410 into capsule 130 thereby releasing the dry powder included therein.

In addition or alternatively, cap 135 can include one or more blades or extensions (not shown) that are configured to puncture the dry powder container at a top or side of the dry powder container (e.g., opposite the bottom side that is be punctured by the puncturing device). In addition, in such a configuration the sidewalls or the extension provided on the cap itself can include one or more openings thereby allowing air to flow through the dry powder container and serves to aid in the evacuation of dry powder from the bottom of the dry powder container when the user inhales from the first end of the inhalation tube.

Figure 7A:
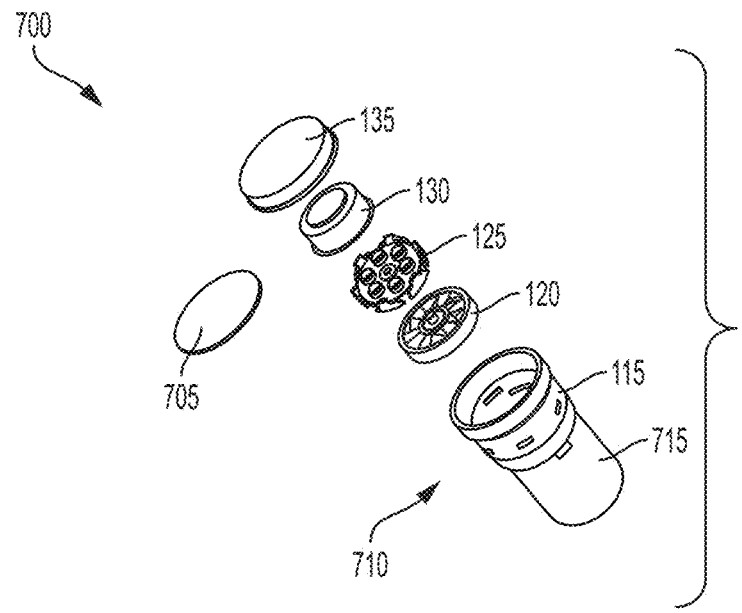
FIG. 7A provides an exploded top perspective view of an alternate exemplary inhalation device in accordance with some embodiments of the present invention.
Figure 7B:
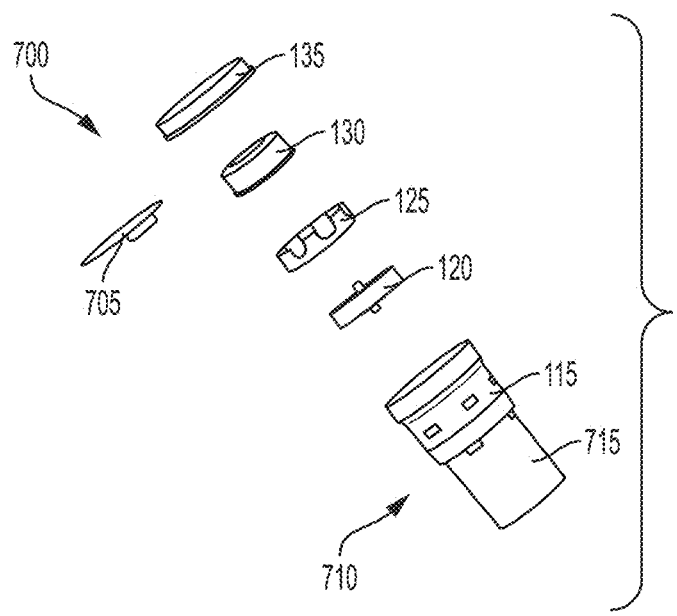
FIG. 7B provides an exploded side perspective view of the alternate exemplary inhalation device of FIG. 7A in accordance with some embodiments of the present invention.
Figure 7C:
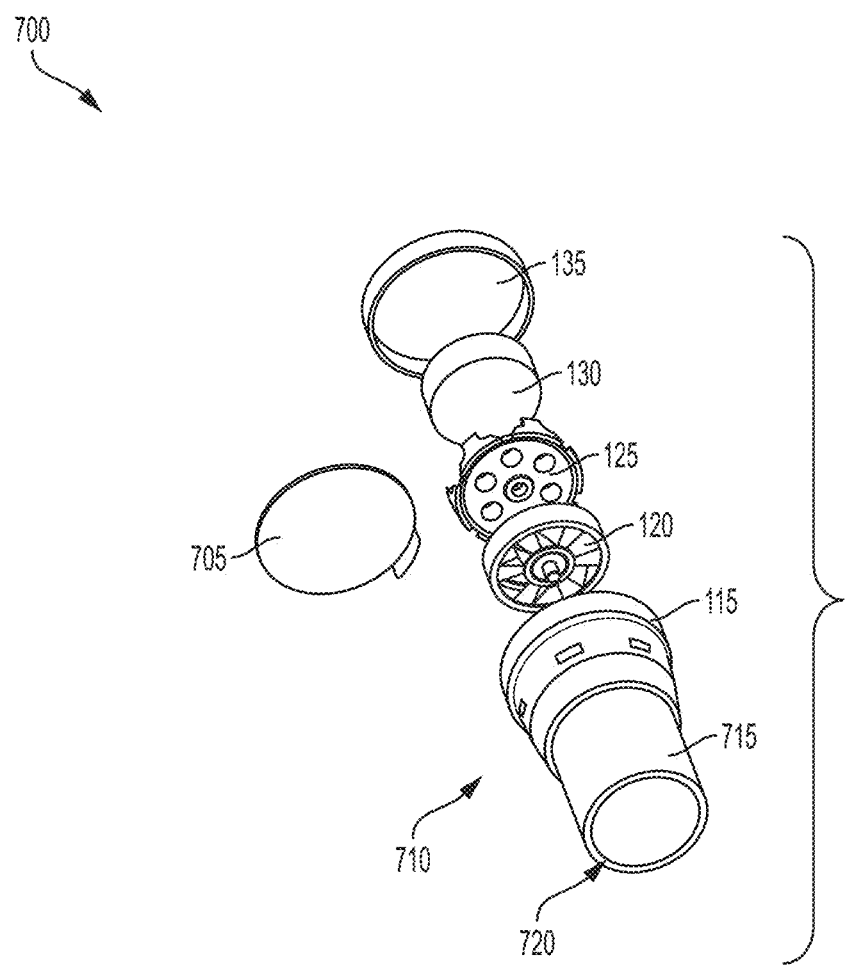
FIG. 7C provides an exploded, bottom-perspective view of the alternate exemplary inhalation device of FIG. 7A in accordance with some embodiments of the present invention.

FIGS. 7A-7C provide exploded views of an alternate exemplary inhalation device 700. When fully assembled, inhalation device 700 includes an inhalation tube assembly 710 that includes an inhalation tube 715 and extension 115, impeller 120, puncturing device 125, dry powder capsule 130, a cover 705, and cap 135.

Exemplary dimensions for the components of dry powder inhaler 100 are as follows:
inhalation tube 715: 15-25 mm in diameter
extension 115: 18-21 mm in length diameter
impeller 120: 16-18 mm in diameter
puncturing device 125: 16-18 mm in diameter
dry powder container 130: 16-18 mm in diameter
cover 705: 16-25 mm in diameter When in use a user may place his or her mouth on an end 720 of inhalation tube 715 and may inhale, or otherwise create a negative pressure, so as to draw the dry powder from the dry powder capsule, which has been punctured by puncturing device directly into the user's mouth and lungs.

Figure 8A:
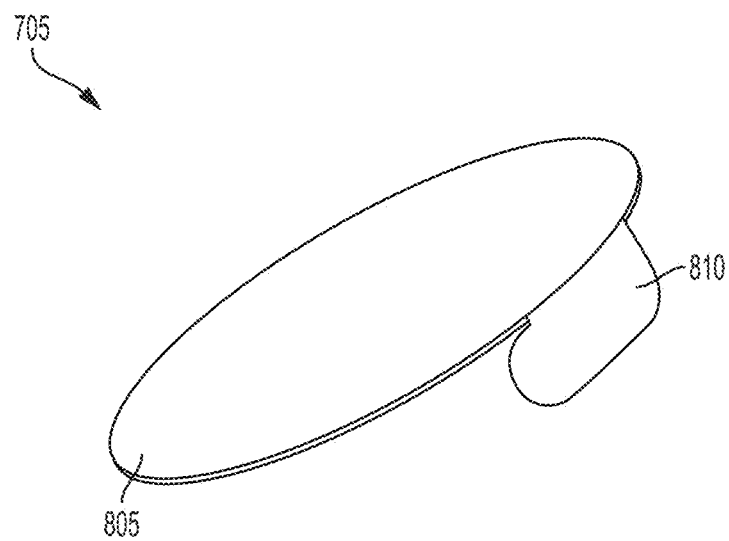
FIG. 8A provides a top-perspective view of a cover in accordance with some embodiments of the present invention.
Figure 8B:
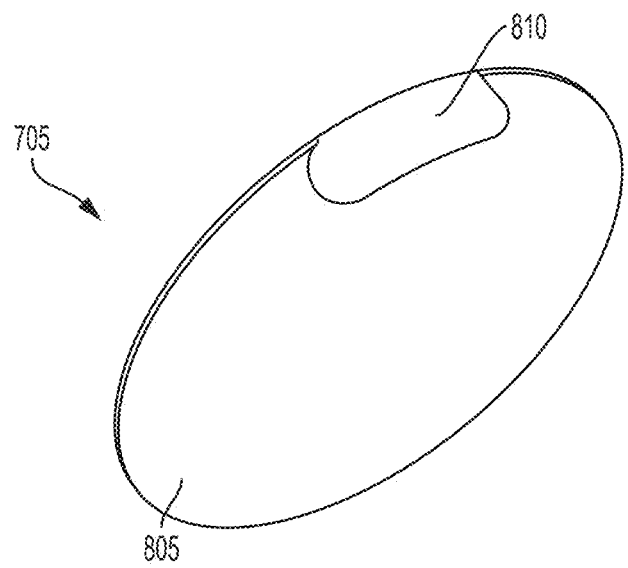
FIG. 8B provides a bottom-perspective view of a cover in accordance with some embodiments of the present invention.

FIG. 8A provides a side perspective view of cover 705 and FIG. 8B provides a bottom perspective view of cover 705. Cover 705 may include a covering or cap portion 805 and a tab or handle 810. In some embodiments, cover 705 may be used in lieu of cap 135. For example, cover 705 may be disposable foil and/or plastic that is removed by a user to access dry powder capsule 130.

Figure 9A:
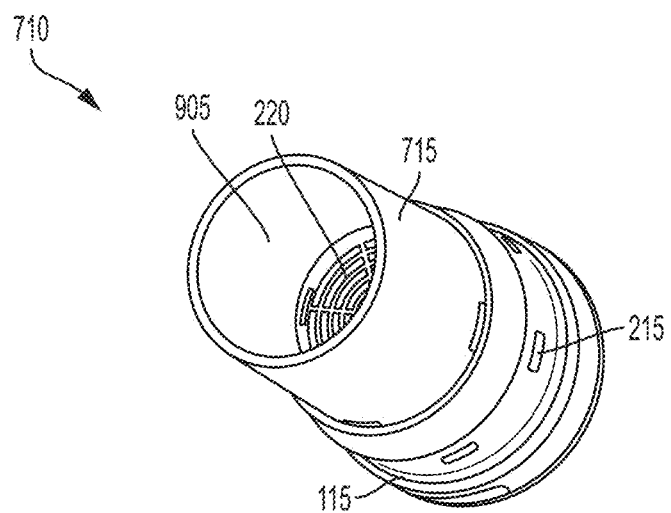
FIG. 9A provides a perspective view of an inhalation tube assembly of the inhalation device of FIG. 7A in accordance with some embodiments of the present invention.

FIGS. 9A-9D provide various views of inhalation tube assembly 710. More specifically, FIG. 9A depicts the bottom of extension 115 and shows a view of grid 220, which has a series of holes or openings 225 that are configured to allow passage of air as well as a dry powder into the inhalation tube 715. Grid 220 also serves to prevent material that exceeds a preferred size from passing through openings 225.

Figure 9B:
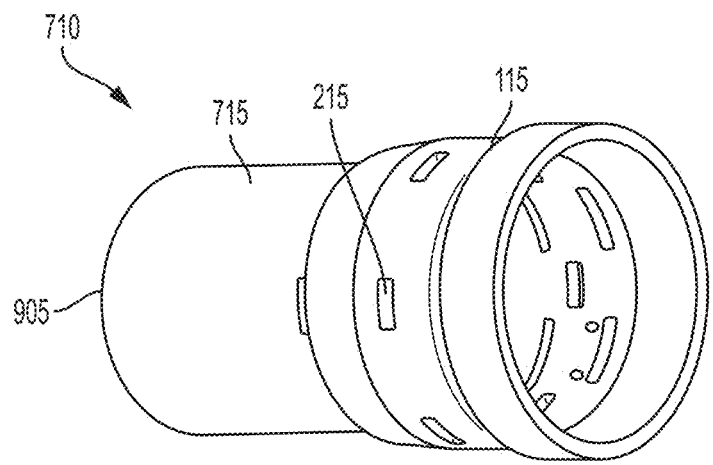
FIG. 9B provides a perspective view of an inhalation tube assembly of the inhalation device of FIG. 7A in accordance with some embodiments of the present invention.

FIG. 9B shows a side plan view of inhalation tube assembly 710 with inhalation tube 715 that includes an open end 905 configured to be inserted into a user's mouth and extension 115 which is configured to accept and house an assembly of impeller 120, puncturing device 125, dry powder capsule 130, cover 705, and cap 135. Inhalation tube 715 is configured without an angle so as to be directly inserted into a user's mouth when the user is, for example, in a supine, or lying down position.

Figure 9C:
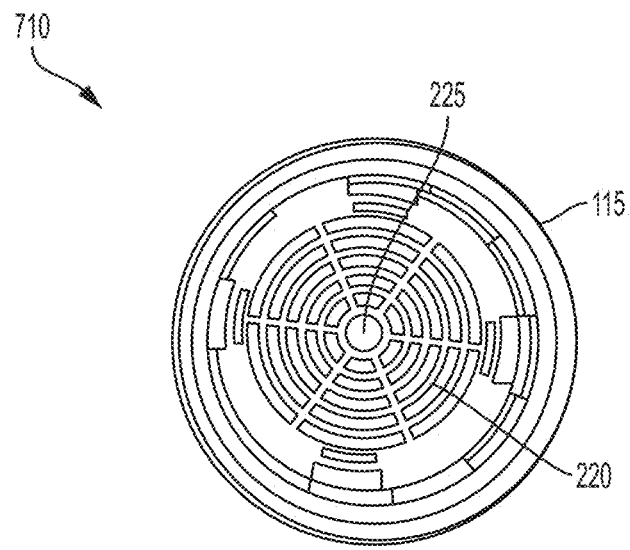
FIG. 9C provides a top view of an inhalation tube assembly of the inhalation device of FIG. 7A in accordance with some embodiments of the present invention.
Figure 9D:
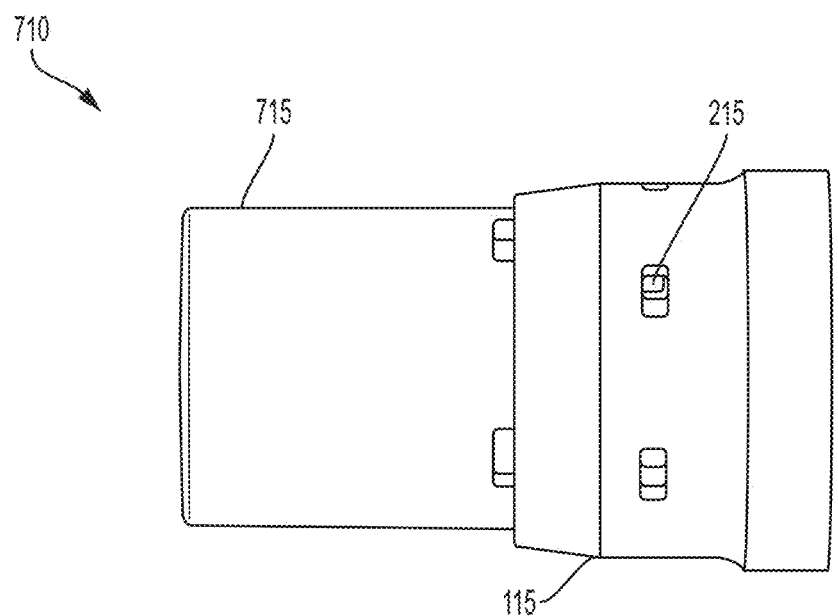
FIG. 9D provides a side view of an inhalation tube assembly of the inhalation device of FIG. 7A in accordance with some embodiments of the present invention.
Figure 10A:
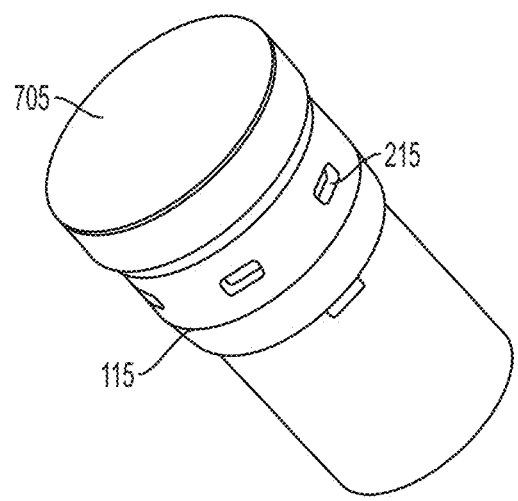
FIG. 10A provides a perspective view of an assembled inhalation device of FIG. 7A in accordance with some embodiments of the present invention.
Figure 10B:
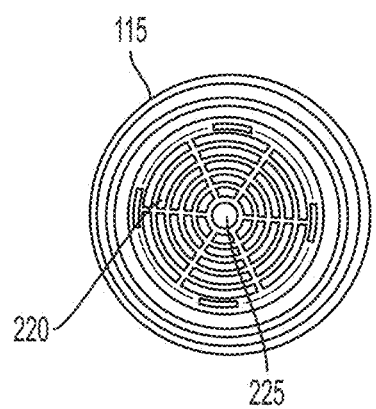
FIG. 10B provides a bottom view of an assembled inhalation device of FIG. 7A in accordance with some embodiments of the present invention.

FIG. 9C provides a bottom perspective view of inhalation tube showing the openings 220 and center opening 225. FIG. 9D shows a side perspective view of inhalation tube 705. FIG. 10A provides a view of an assembled inhalation device 700 without cap 135. Stated differently, the assembled inhalation device 700 of FIG. 10A includes the assembly of impeller 120, puncturing device 125, dry powder capsule 130, and cover 705. FIG. 10B provides a bottom plan view of inhalation device 700, which shows openings 220 as well as the axis pin of impeller 305 inserted into center opening 225.

Figure 11A:
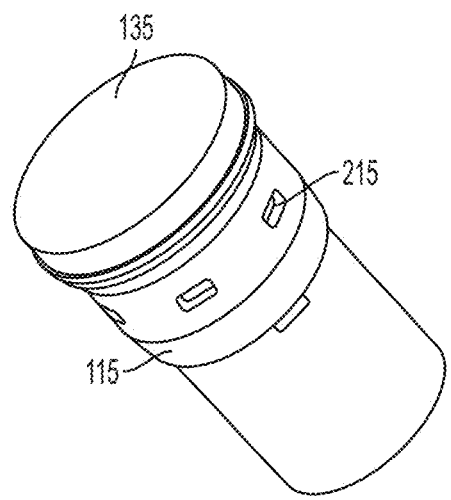
FIG. 11A provides a top perspective view of an assembled inhalation device of FIG. 7A in accordance with some embodiments of the present invention.
Figure 11B:
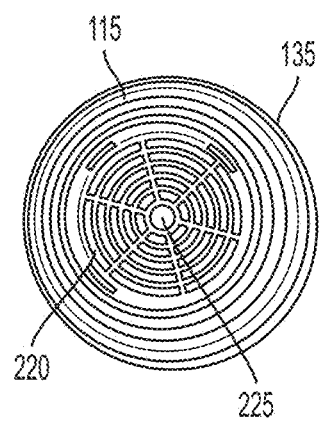
FIG. 11B provides a bottom view of an assembled inhalation device of FIG. 7A in accordance with some embodiments of the present invention.

FIG. 11A provides a view of an assembled inhalation device 700 with cap 135. Stated differently, the assembled inhalation device 700 of FIG. 10A includes the assembly of impeller 120, puncturing device 125, dry powder capsule 130, cover 705, and cap 135. FIG. 11B provides a bottom plan view of inhalation device 700, which shows openings 220 as well as the axis pin of impeller 305 inserted into center opening 225 and the bottom of cap 135.

Figure 12A:
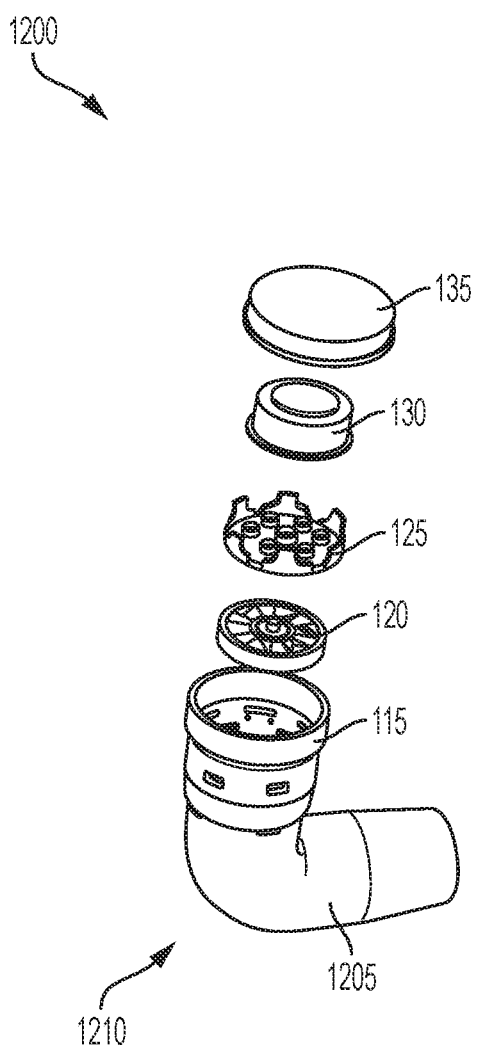
FIG. 12A provides an exploded perspective view of another exemplary inhalation device in accordance with some embodiments of the present invention.
Figure 12B:
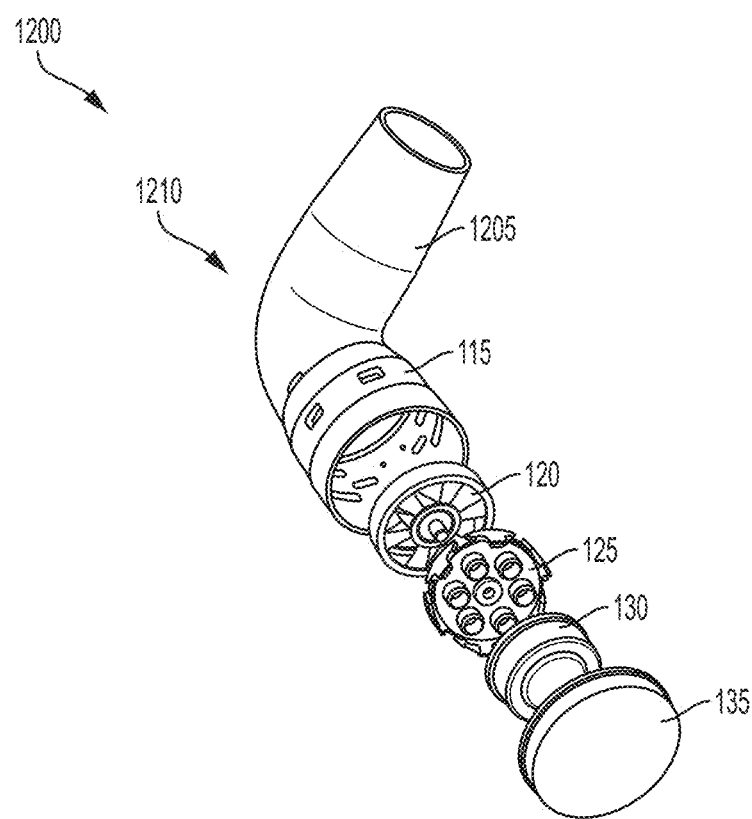
FIG. 12B provides an exploded perspective view of the another exemplary inhalation device of FIG. 12A in accordance with some embodiments of the present invention.
Figure 13A:
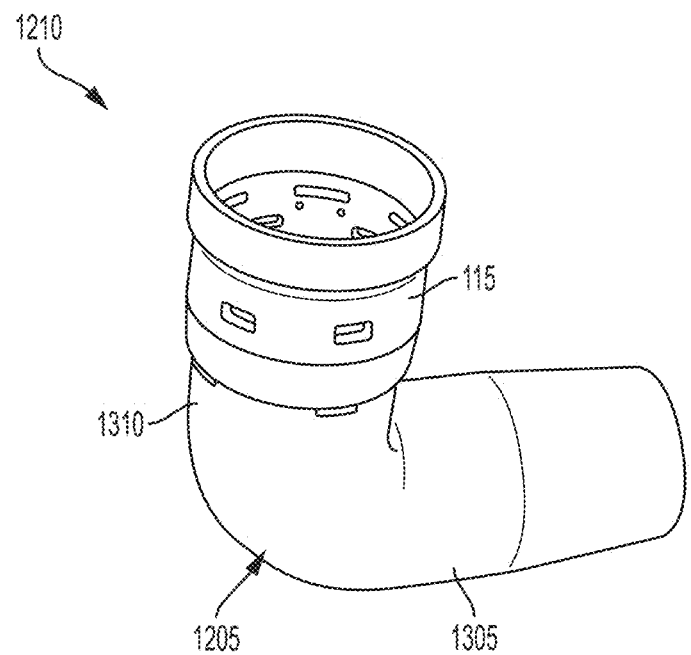
FIG. 13A provides a perspective view of a right angle inhalation tube assembly of the inhalation device of FIG. 12A in accordance with some embodiments of the present invention.
Figure 13B:
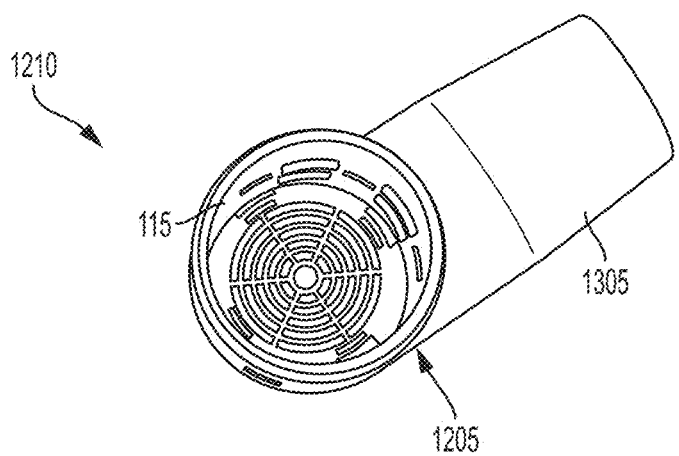
FIG. 13B provides a top view of a right angle inhalation tube assembly of the inhalation device of FIG. 12A in accordance with some embodiments of the present invention.
Figure 13C:
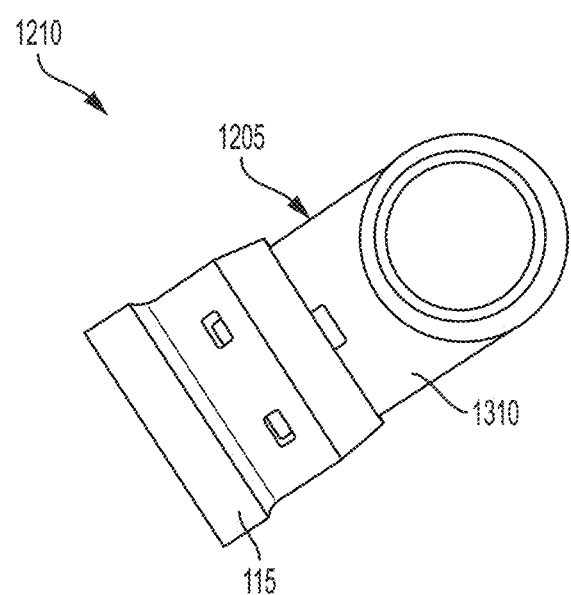
FIG. 13C provides a front view of a right angle inhalation tube assembly of the inhalation device of FIG. 12A in accordance with some embodiments of the present invention.
Figure 14A:
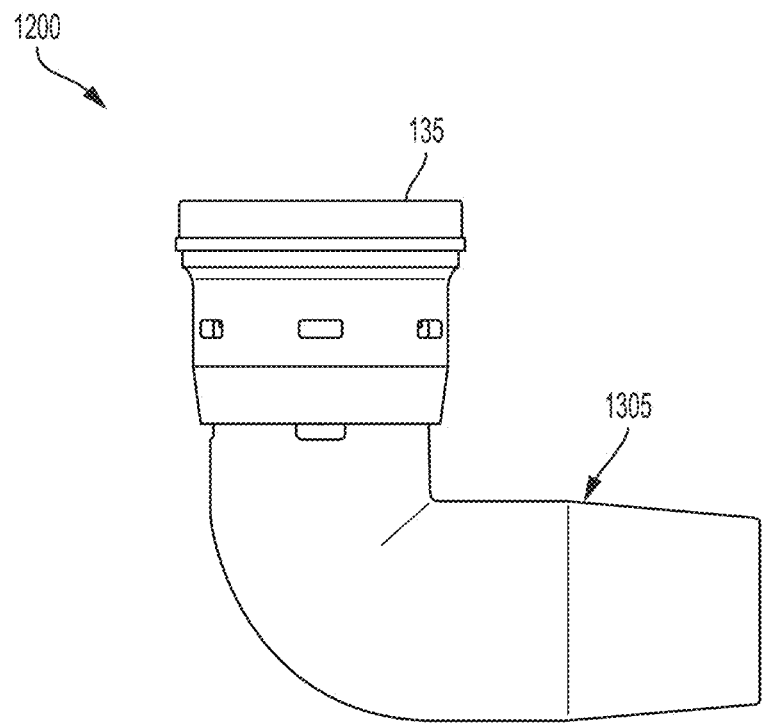
FIG. 14A provides a side view of an assembled dry powder inhaler of FIG. 12A in accordance with some embodiments of the present invention.
Figure 14B:
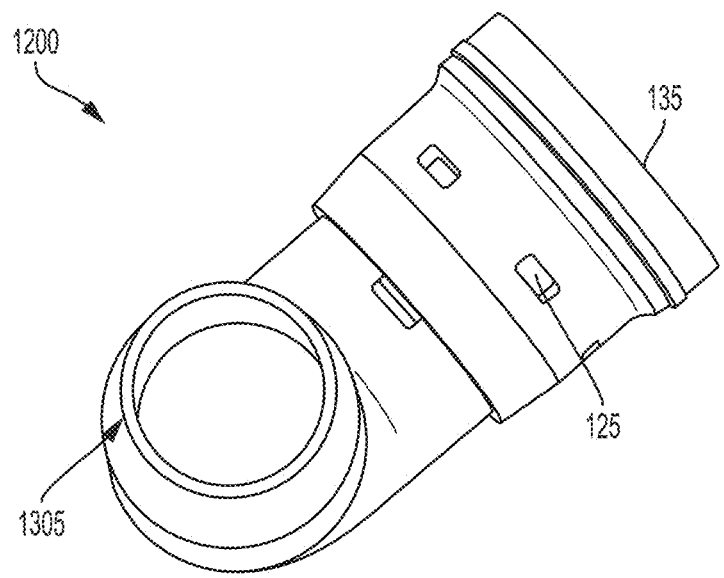
FIG. 14B provides a front perspective view of an assembled dry powder inhaler of FIG. 12A in accordance with some embodiments of the present invention.

FIGS. 12A and 12B depict exploded views of another exemplary inhalation device 1200. FIG. 12A provides a side exploded view of inhalation device 1200 and FIG. 12B provides a lower perspective exploded view of inhalation device 1200. Inhalation device 1200 includes extension 115, impeller 120, puncturing device 125, dry powder capsule 130, and cap 135. Inhalation device 1200 also includes a right angle inhalation tube assembly 1210 with a right angle inhalation tube 1205 and extension 115. FIG. 14A provides a side view of an assembled dry powder inhaler of FIG. 12A in accordance with some embodiments of the present invention; FIG. 14B provides a front perspective view of an assembled dry powder inhaler of FIG. 12A in accordance with some embodiments of the present invention;

Exemplary dimensions for the components of dry powder inhaler 100 are as follows:
  right angle inhalation tube 1205 (lower portion): 40-50 mm in length
  right angle inhalation tube 1205 (upper portion): 25-35 mm in length
  extension 115: 18-21 mm in diameter
  impeller 120: 16-18 mm in diameter
  puncturing device 125: 16-18 mm in diameter
  dry powder container 130: 16-18 mm in diameter FIGS. 13A-13C provide various views of right angle inhalation tube assembly 1210. FIG. 13A depicts a side perspective view of inhalation tube assembly 1210 and shows the length of a lower right angle extension 1305 of right angle inhalation tube 1205 is slightly longer than the length of the combination of extension 115 and upper right angle extension 1310 of right angle inhalation tube 1205. FIG. 13B shows a top plan view of right angle inhalation tube assembly 1210 and FIG. 13C shows a side perspective view of right angle inhalation tube assembly 1210.

As noted, a variety of impeller and/or propeller designs can be implemented to assist the flow of air and dry powder through the interior volume of the inhalation device during use without departing from the scope of the exemplary embodiments. In accordance with these and other aspects of the invention, additional configurations and variations of the disclosed dry powder inhalation devices are further described herein.

Figure 16A:
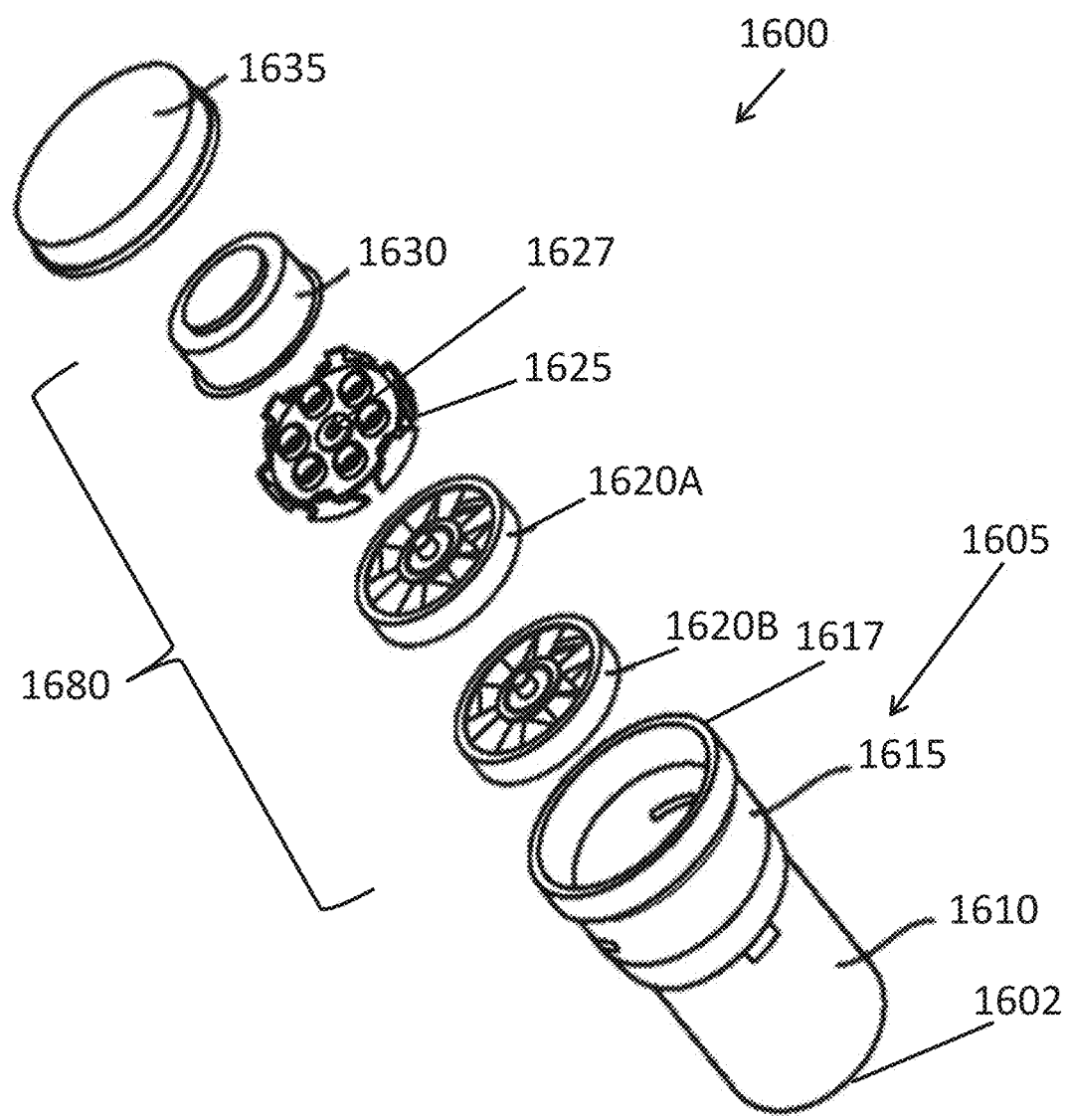
FIG. 16A provides a perspective side view of an exploded dry powder inhaler in accordance with some embodiments of the present invention.

FIG. 16A depicts an exploded side-perspective view of an exemplary dry powder inhaler 1600 that utilizes multiple impellers to facilitate the administration of medication in accordance with one or more of the exemplary embodiments. As shown, the dry powder inhaler 1600 includes an inhaler body 1605 comprising an inhalation tube 1610, which has a first end 1602 and an extension 1615 that extends from the opposing end of the inhalation tube. The inhaler body can be comprised of a single continuous structure or one or more individual components (e.g., inhaler body and extension) that are fixedly or removably joined to define the inhaler body. Similarly, the extension and/or inhaler body can be comprised of a single continuous structure or one or more individual components. In addition, in some instances, the extension can be at least partially defined by a portion of the inhalation tube and vice versa.

In the particular configuration shown in FIG. 16A, the extension 1615 and inhalation tube 1610 both have a generally circular cross-sectional profile and are linearly arranged such that the internal volume bounded by the extension and inhalation tube extends axially from a top end 1617 of the extension to the bottom end 1602 of the inhalation tube. As noted previously, it should be appreciated that the cross-sectional profile and overall shape of the dry powder inhaler and the components thereof (e.g., inhaler body, inhalation tube, extension, impeller(s), puncturing device(s), and/or dry powder container) can have alternative shapes and sizes without departing from the scope of the invention disclosed herein. For example and without limitation, the inhaler body can have an overall "L" shape or "T" shape and the like.

The exemplary inhaler 1600 also includes an assembly 1680 of components including dry powder container 1630, and two impellers 1620A and 1620B. As shown, the assembly can also include a puncturing device 1625. The components can be arranged generally in series, and the assembly 1680 can be positioned within the internal volume of the inhaler body 1605. More specifically, one or more of the components of the assembly can be disposed within the internal volume of the extension 1615 and/or the inhalation tube 1610 or a combination of the foregoing. For example and without limitation, the components of the assembly can all be located within the extension. By way of further example, one or more components, say, the dry powder container, the puncturing device and a first impeller 1620A can be located within the extension and the second impeller 1620B can be located within the inhalation tube 1610.

Preferably, the extension 1615 and/or the inhalation tube 1610 is sized and configured to accept one or more components of the assembly 1680 therein. Accordingly, in some embodiments, the components of the assembly (i.e., the impellers, the puncturing device, and the dry powder container) can be shaped and sized so as to fit at respective positions within the inhaler body 1605. For instance, the impellers 1620A/B and dry powder container 1630 can have a generally circular shape (when viewed from a top or bottom perspective) so as to fit within inside the generally tube-like inhaler body.

As noted, in some implementations, one or more of the components of the assembly 1680 can be configured to fit together with one another. In addition or alternatively, one or more components of the assembly can be independently positioned and mounted within the inhaler body.

In some implementations, the puncturing device 1625 can be provided to puncture the dry powder container 1630 prior to use thereby allowing the medication contained therein to be released. For instance, as shown in FIG. 16A, the puncturing device can be disposed beneath the dry powder container so as to puncture the bottom of the dry powder container. In addition or alternatively a puncturing device can be provided to puncture the top or even sides of the dry powder container so as to facilitate air flow through the dry powder container. It should be appreciated that alternative designs and methods for providing openings in one or more walls of the dry powder container to facilitate the release of medication can be implemented without departing from the scope of the invention. In addition, optionally, a cap 1635 can also be placed over the top end 1617 of the extension so as to, for example, secure the assembly 1680 within the inhaler body 1605 before/after use and, further optionally, during use of the dry powder inhaler.

According to a salient aspect, the exemplary dry powder inhaler 1600 includes multiple impellers, namely, 1620A and 1620B. In the particular embodiment depicted in FIG. 16A, when the assembly 1680 is positioned within the internal volume of the inhaler body 1605, the two impellers are located below the dry powder container 1630 (i.e., between the bottom side of the dry powder container and the first end 1602 of the inhalation tube 1610). For clarity, in this particular configuration, the impellers are arranged in series.

As noted, each impeller may have a number of blades (e.g., 6, 8, 10, etc.) provided in a variety of different patterns. Each blade can be adjacent to a corresponding opening. The impeller and the blades can be positioned such that, when a user applies a negative pressure to the first end 1602 of the inhalation tube (for example, by the user inhaling from the first end) and draws air through the inhalation tube, a force or pressure differential is applied to the impellers causing the impellers to rotate about their respective central axes which serves to assist in the evacuation of dry powder from the dry powder container 1630 and direct the powder through the interior volume toward the first end 1602 (i.e., in "the longitudinal direction") so that the dry powder can be inhaled by the user. Thus, the impellers are configured to facilitate the axial flow of air and medication through the impellers and the internal volume of the inhaler body 1605 in the longitudinal direction. In some embodiments, the impellers can be configured to aerosolize the dry powder to facilitate the evacuation of the dry powder from the dry powder container 1630 and further directs it through the inhaler body 1605 toward the first end 1605.

In some implementations, the impellers 1620A and 1620B are configured to rotate in the same direction. In some implementations, the two impellers can be counter-rotating (i.e., rotating in opposite directions), however, preferably, the overall direction of air-flow through the inhaler body 1605 is in the longitudinal direction (i.e., toward the first end 1602).

It should be understood that a variety of impeller and/or propeller designs can be implemented to assist the flow of air and dry powder through the interior volume of the inhalation device during use without departing from the scope of the exemplary embodiments. For instance, the various configurations discussed in connection with FIGS. 3A-3C above.

Although not shown in FIG. 16A, the impellers can be mounted in respective positions within the internal volume of the inhaler body by one or more mounts. As noted, the one or more mounts can be structures that are coupled to or integrally formed with the inhaler body 1605. For instance, mount structure having a central mounting hole (not shown) can be provided below the bottom impeller 1620B and can be configured to receive an axis pin of the impeller within the mounting hole such that impeller 1620B is supported from the underside. A mount can similarly be provided to locate and support an impeller from a top side as well. By way of further example, the mount can be integrated into a component of the assembly 1680 that is adjacent to an impeller. For instance, as shown in FIG. 16A, the puncturing device 1625 can include a central mounting hole 1627 that is sized and shaped to receive a top end of the axis pin of impeller 1620A.

As noted, in some implementations, the mount(s) supporting an impeller can be configured such that the impeller and central axis pin can freely rotate relative to the mount(s). In other implementations, an axis pin extending axially through the center of the impeller can be fixedly mounted to the one or more mounts and the impeller can be configured to rotate about the central axis pin, for instance, using a bearing assembly sealed within the impeller and surrounding the central axis pin.

Figure 16B:
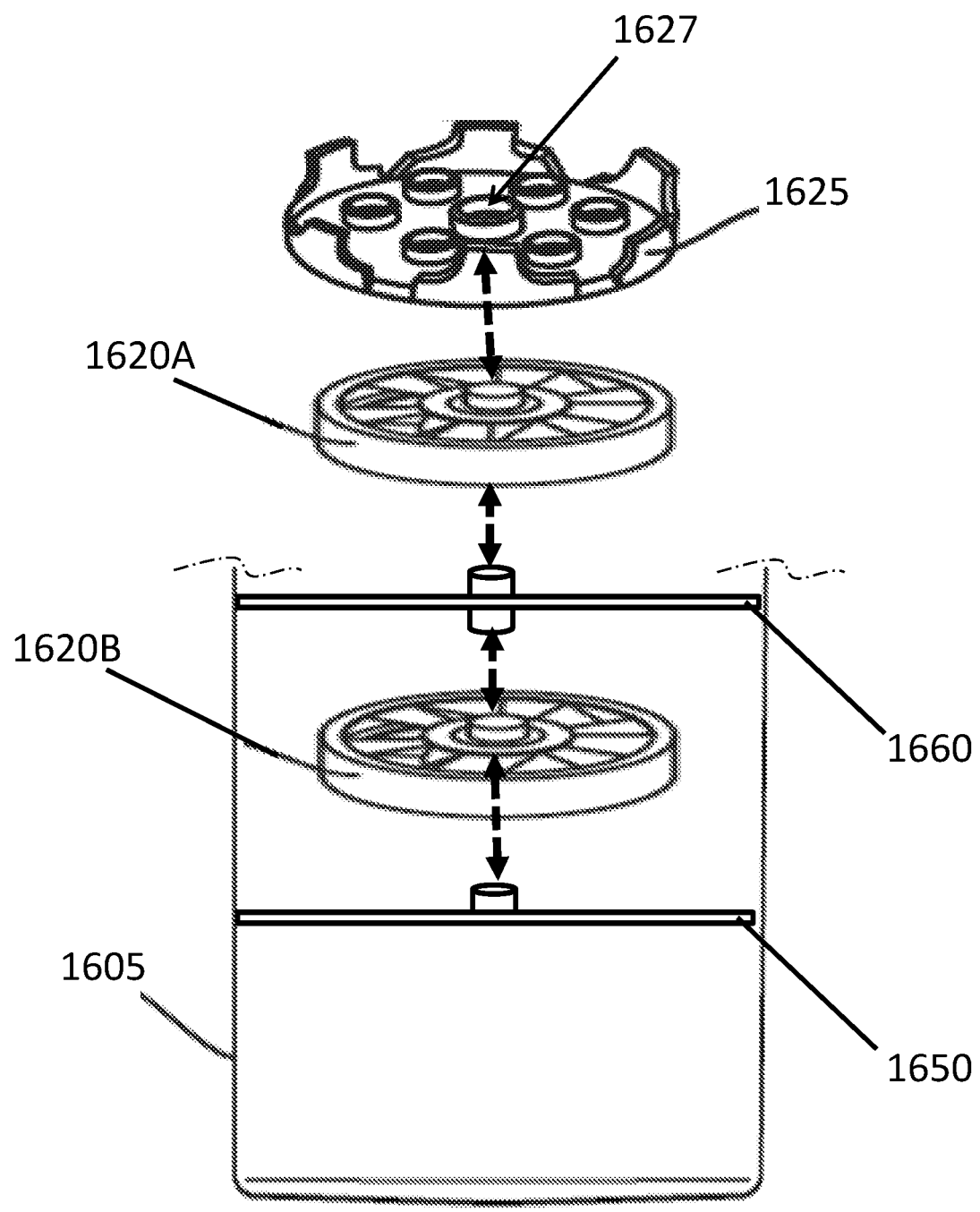
FIG. 16B provides a side view of an exploded dry powder inhaler in accordance with some embodiments of the present invention.

In some implementations, the one or more mounts can be configured to position/support a single component of the assembly 1680 (e.g., a single impeller). In addition or alternatively, the one or more mounts can be configured to support multiple components of the assembly (e.g., multiple impellers). FIG. 16B is a simplified diagram illustrating an exemplary configuration in which impellers 1620A and 1620B, which are independently rotating, from above using the puncturing device 1625, from below using a bottom mount structure 1650, and from between using central mount structure 1660.

Figure 16C:
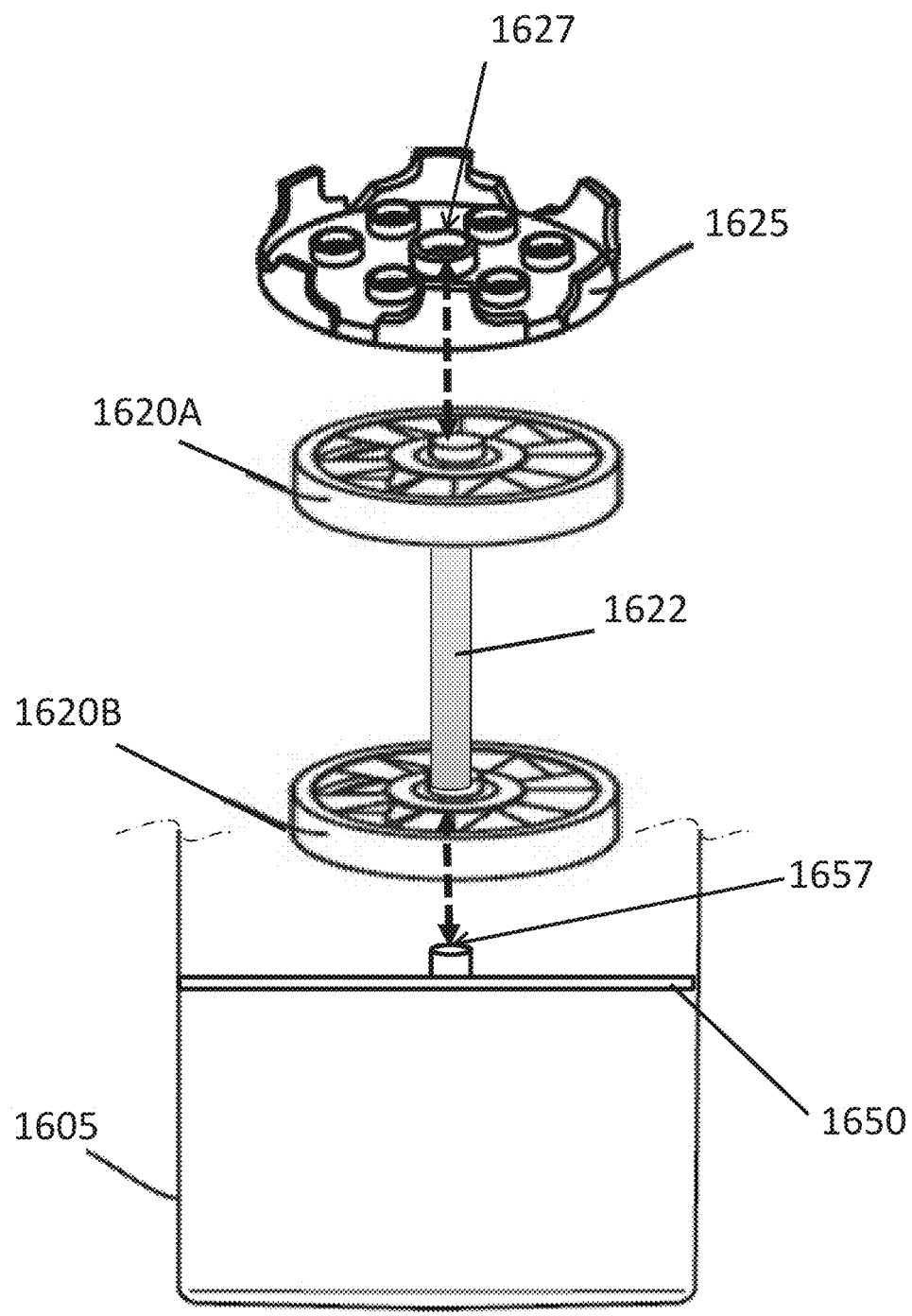
FIG. 16C provides a side view of an exploded dry powder inhaler in accordance with some embodiments of the present invention.

In some implementations, the one or more mounts can be provided to support multiple impellers that are joined together as an assembly. For instance, FIG. 16C is a simplified diagram illustrating an exemplary configuration in which impellers 1620A and 1620B define an assembly 1680 that is supported from above by the puncturing device 1625 and supported from below by a bottom mount structure 1650. In the particular implementation shown, impellers 1620A and 1620B are joined by a common central axis pin 1622, puncturing device 1625 includes a central mounting hole 1627 configured to receive a top end of the central axis pin 1622 and the bottom mount structure 1650 includes a central mounting hole 1657 for receiving a bottom end of the central axis pin. Although only a cut-away lower portion of the inhaler body 1605 is shown in the side view of FIG. 16C, it should be understood that the bottom mount structure can be configured to extend from the walls of the inhaler body across the internal cross-section in a manner that does not obstruct air flow in the longitudinal direction. As noted, the impellers and mounting holes can be configured such that the axis pin rotates within the mounting holes 1657 and 1627 enabling the two impellers to rotate together. However, in addition or alternatively, the common axis pin can be immovably held by the mounting holes 1657 and 1627 and the impellers can be configured to rotate independently about the axis pin.

Figure 16D:
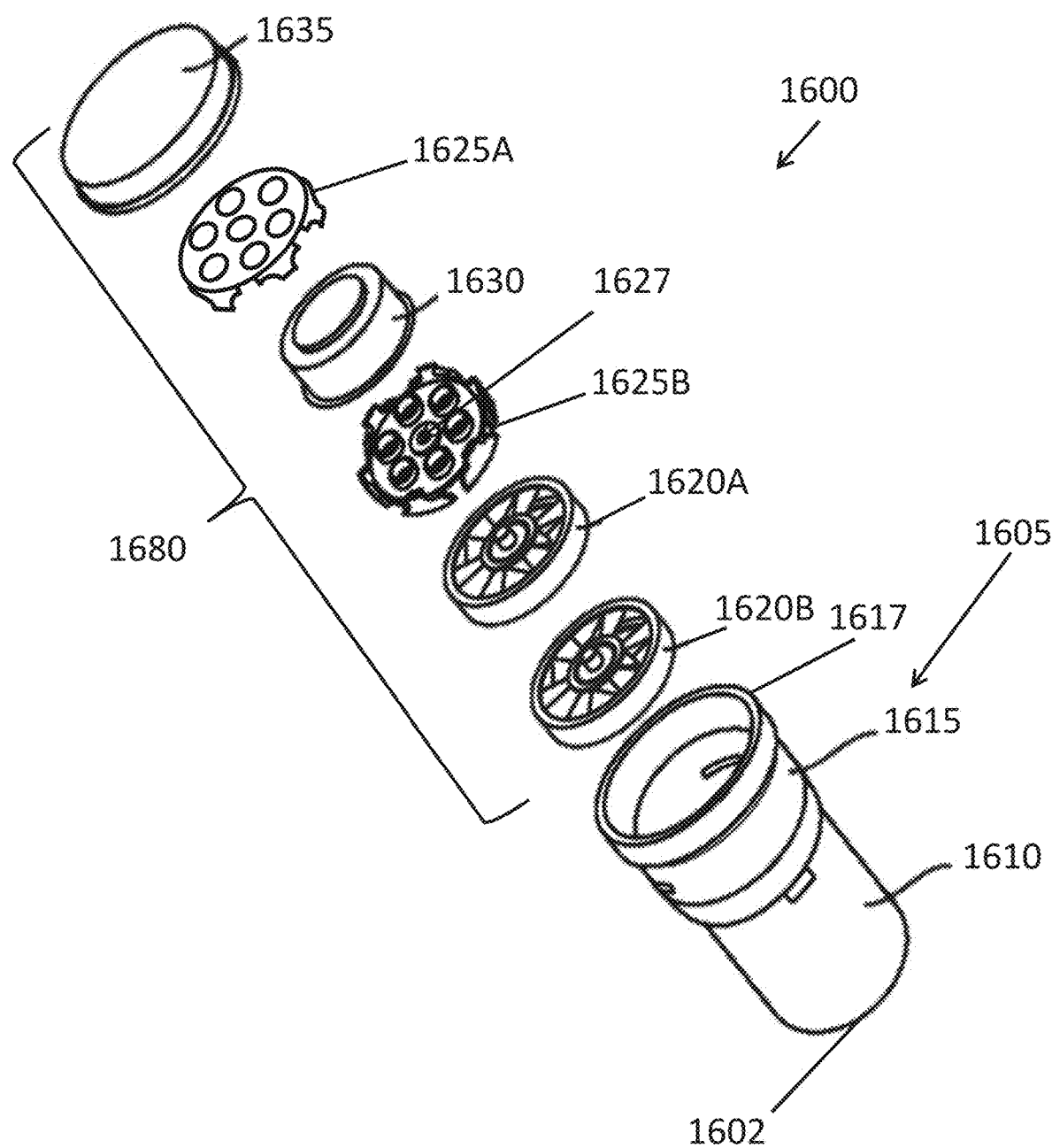
FIG. 16D provides a side view of an exploded dry powder inhaler in accordance with some embodiments of the present invention.

In some embodiments, the dry powder inhaler 1600 may utilize multiple puncturing devices 1625 and multiple impellers 1620, an exemplary example is shown in FIG. 16D. A capsule 1630 is arranged between two puncturing devices 1625A and 1625B with both extensions facing the capsule to facilitate penetration to the capsule.

Figure 17A:
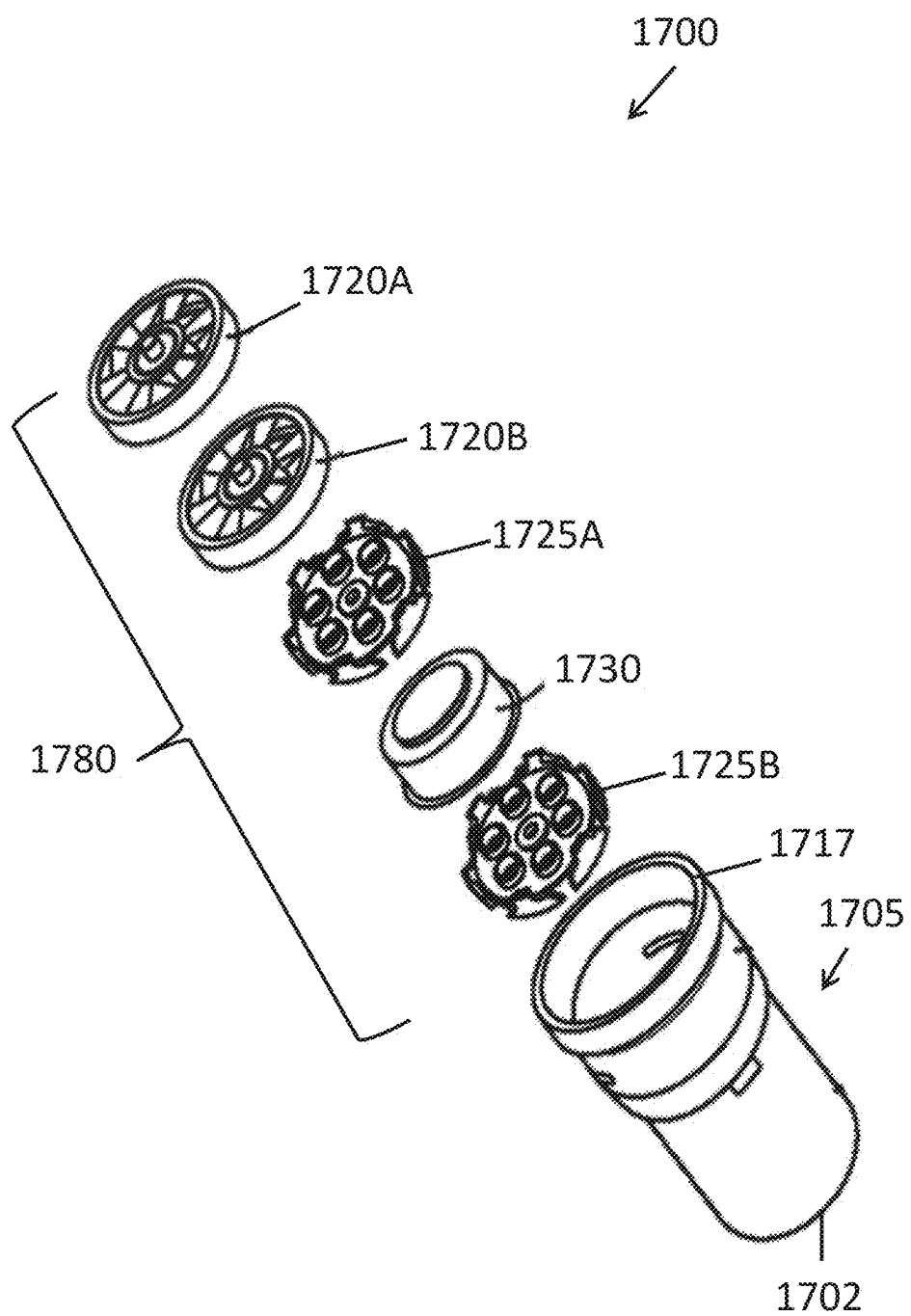
FIG. 17A provides a perspective side view of an exploded dry powder inhaler in accordance with some embodiments of the present invention.

FIG. 17A is an exploded side-perspective view of another exemplary configuration of a dry powder inhaler in accordance with one or more embodiments of the invention. FIG. 17A depicts a dry powder inhaler 1700 that includes an inhaler body 1705 configured to receive an assembly 1780 of components therein. The assembly of components are shown in an exploded view in FIG. 17A and includes impellers 1720A and 1720B, a dry powder container 1730, and puncturing devices 1725A and 1725B.

Figure 17B:
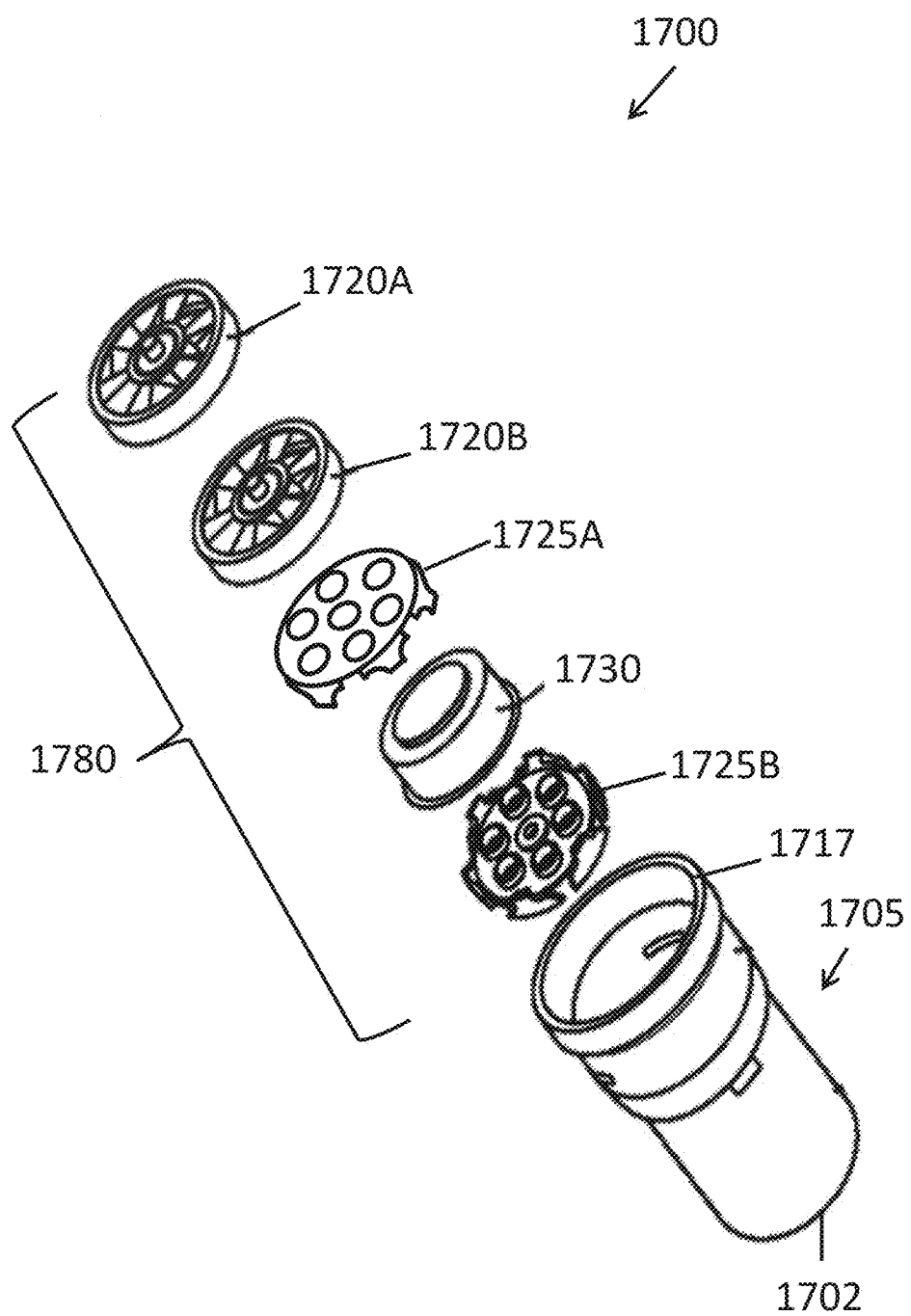
FIG. 17B provides a perspective side view of an exploded dry powder inhaler in accordance with some embodiments of the present invention.

FIG. 17B is an exploded side-perspective view of another exemplary configuration of the dry powder inhaler shown in FIG. 17A, where the puncturing device 1625A is configured to have its extensions facing the capsule to facilitate penetration to the capsule.

Figure 17C:
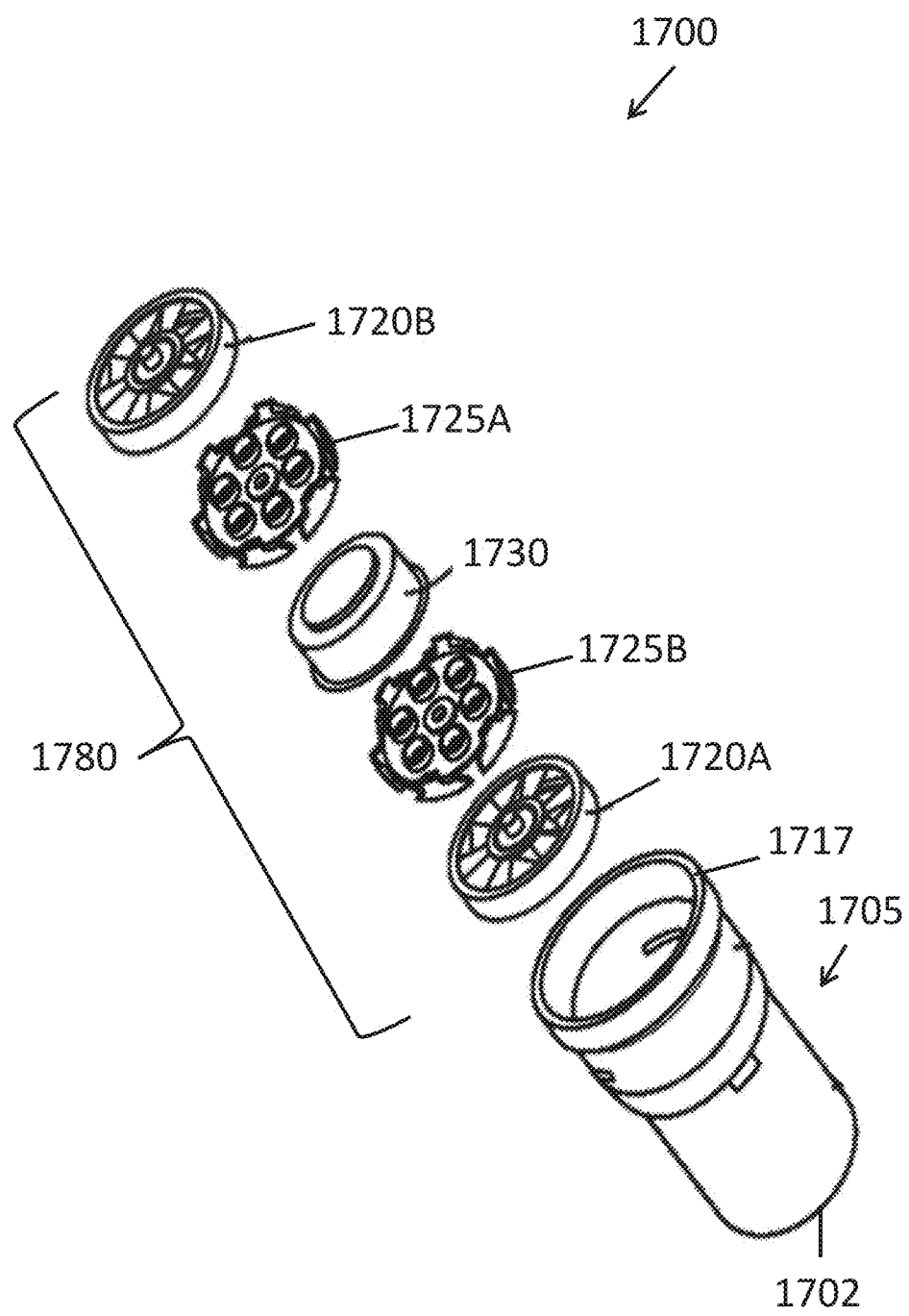
FIG. 17C provides a perspective side view of an exploded dry powder inhaler in accordance with some embodiments of the present invention.
Figure 17D:
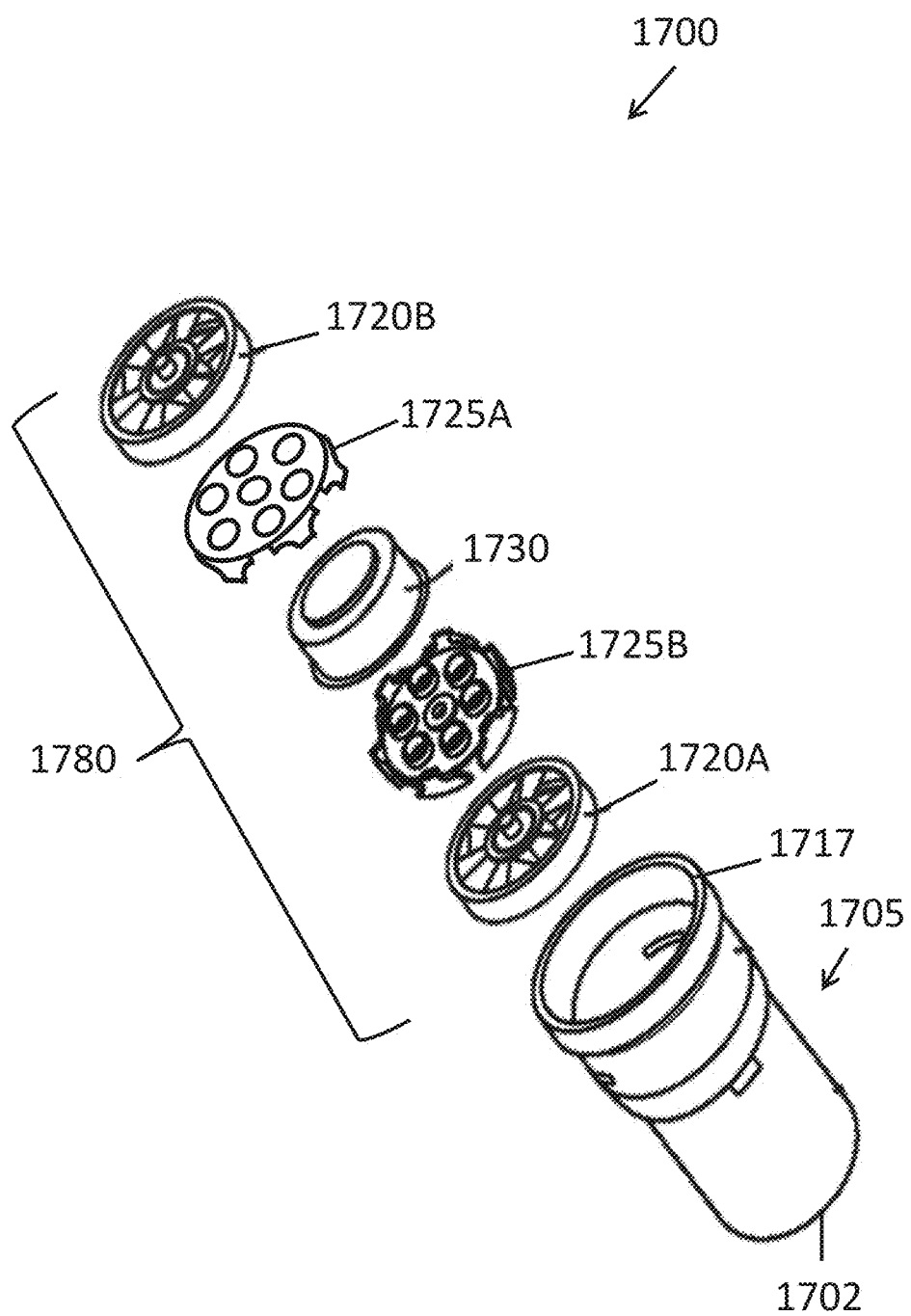
FIG. 17D provides a perspective side view of an exploded dry powder inhaler in accordance with some embodiments of the present invention.

FIGS. 17C and 17D are an exploded side-perspective view of another exemplary configuration of the dry powder inhaler shown in FIGS. 17A and 17B, respectively, wherein one of the multiple impeller is positioned below the capsule 1630.

Whereas the exemplary inhalation device 1600 shown in FIG. 16A includes two impellers placed below the dry powder container within the device body and are configured to draw air and/or powder from the bottom of the dry powder container and direct it toward the first end, the inhalation device 1700 includes two impellers 1720A and 1720B that are positioned within the inhaler body 1750 above the dry-powder container 1730 (relative to the first end 1702) and are configured to facilitate the evacuation of the dry powder by directing air flow through the dry powder container and toward the opposite first end 1702 of the inhaler body.

In particular, the impellers 1720A and 1720B and their respective blades can be positioned such that, when a user applies a negative pressure to the first end 1702 of the inhalation tube and draws air through the inhalation tube, a force or pressure differential is applied to the impellers causing the impellers to rotate about their respective central axes which serves to direct air through the dry-powder container and effectively push the air and powder longitudinally through the interior volume toward the first end 1702.

As shown in FIG. 16A, puncturing devices 1725A and 1725B can be provided above and below the dry powder container 1730, respectively, so as to puncture the top and bottom walls of the dry powder container and thereby facilitate the flow of air therethrough.

Figure 18A:
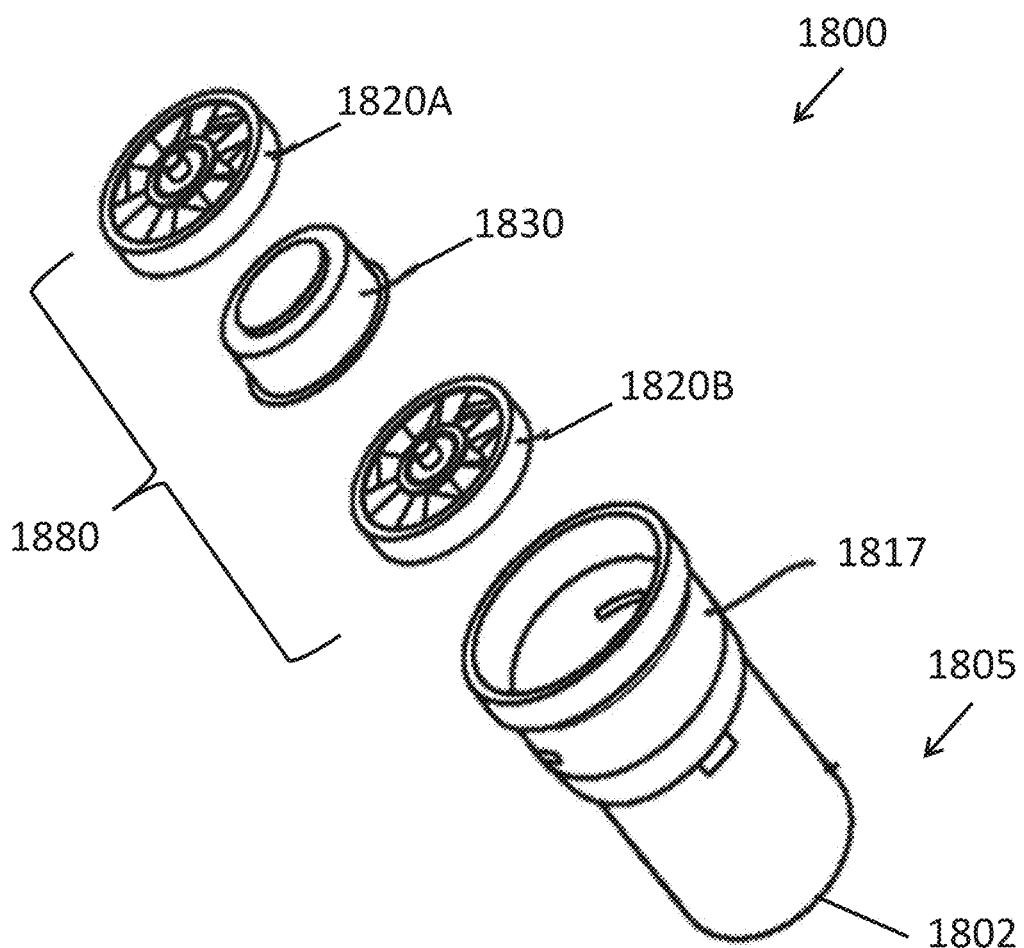
FIG. 18A provides a perspective side view of an exploded dry powder inhaler in accordance with some embodiments of the present invention.
Figure 18B:
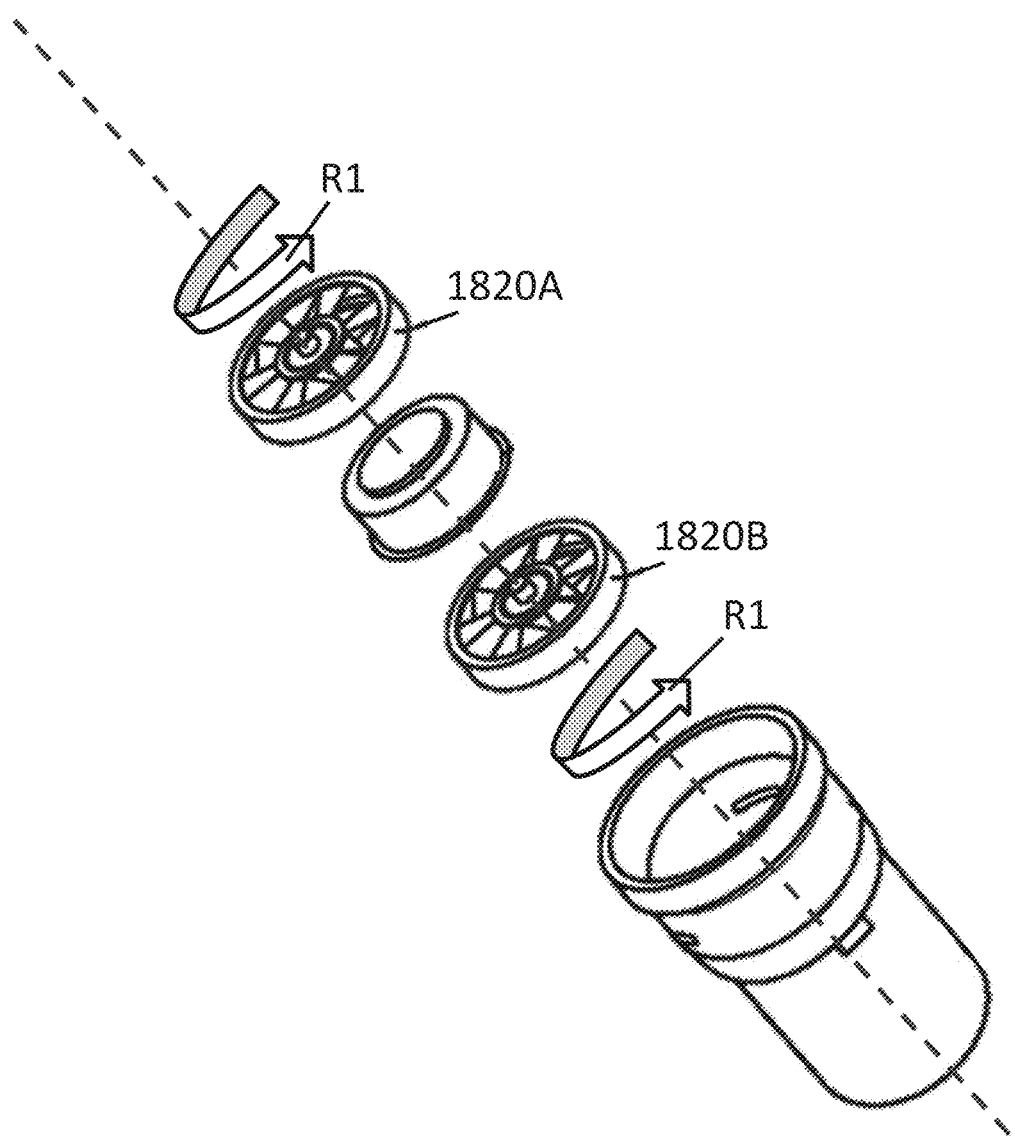
FIG. 18B provides a perspective side view of an exploded dry powder inhaler in accordance with some embodiments of the present invention.
Figure 18C:
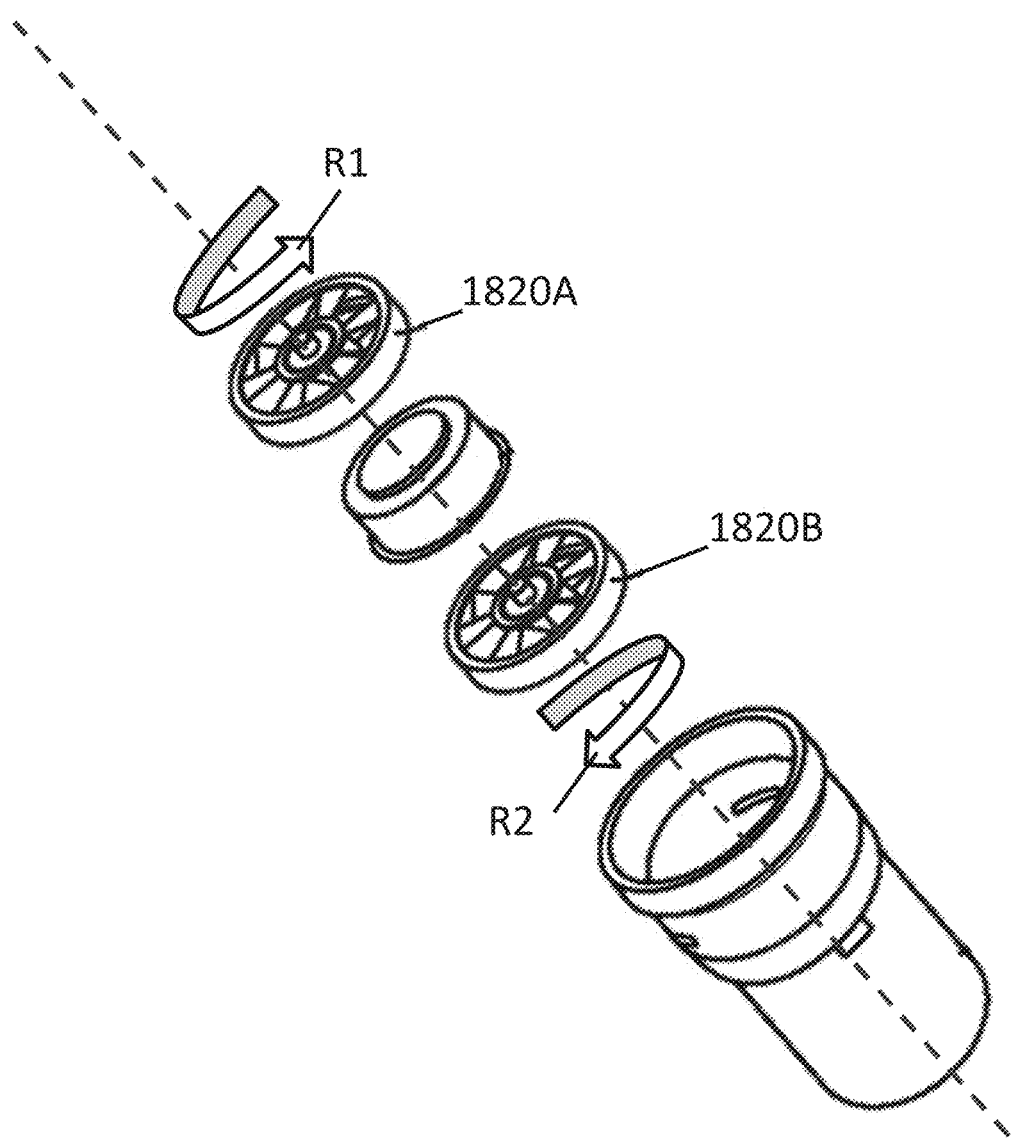
FIG. 18C provides a perspective side view of an exploded dry powder inhaler in accordance with some embodiments of the present invention.

FIG. 18A-18C are a simplified exploded side-perspective view diagrams of an exemplary dry powder inhaler 1800 in accordance with one or more embodiments of the invention. As shown, the dry powder inhaler 1800 can include an inhaler body 1805 having a first end 1802 and second end 1817 and that is configured to receive an assembly 1880 therein. The assembly comprises components arranged in series including, for example and without limitation, a dry powder container 1830 and impellers 1820A and 1820B, which are respectively located above and below the dry powder container within the interior volume of the inhaler body.

As described previously, when air is drawn through the inhaler body 1805 from the first end 1802, the impeller 1820B, which is positioned below the dry powder container within the internal volume of the inhaler body 1805 can be configured to rotate. As a result the impeller 1820B can facilitate the evacuation of powder through the perforated bottom side of the dry powder container and direct the flow of air and powder toward the first end 1802. Similarly, as noted above, when a negative pressure is provided at the first end 1802, the resulting pressure differential across the impeller 1820A, which is positioned above the dry powder container, can cause the impeller to rotate and thereby push air through perforations in a top side of the dry powder container and further facilitates the evacuation of powder from the container and the axial flow of air and medication toward the first end 1802.

Although not shown in FIG. 18A, it should be understood that the assembly 1880 can include one or more puncturing devices or other such means for providing openings in the dry powder container 1830 so as to facilitate airflow through the dry powder container in the longitudinal direction. Similarly, although not shown in FIG. 18, it should also be understood that the dry powder inhaler 1800 can include one or more mounts configured to support and locate one or more of the impellers 1820A and 1820B as well as other components of the assembly 1880 housed within the inhaler body 1805.

In some implementations, the multiple impellers can be configured to rotate in the same direction, counter rotating directions and a combination of the foregoing. For instance, FIG. 18B illustrates impellers 1820A and 1820B rotating in the same rotational direction R1 and FIG. 18C illustrates impellers 1820A and 1820B rotating in opposite rotational directions identified by arrows R1 and R2. Accordingly, it should be appreciated that the exemplary inhaler devices described in connection with FIGS. 16A-16C and 17, can be similarly configured to have multiple impellers rotating in one or more rotational directions.

Moreover, while the exemplary dry powder inhalation devices described above have been described as including one or two impellers provided above, below, or above and below a dry powder container, it should be appreciated that any number of impellers, dry powder containers and puncturing devices can be used. For instance, one or more impellers can be provided above a dry powder container and configured to push air through the container or none at all. Similarly one or more impellers can be positioned below a dry powder container so as to draw air and medication from the container, or none at all. However, the net air-flow through the body of the exemplary dry powder inhalers is preferably in the longitudinal direction (i.e., toward the end that the user is drawing air from).

As noted, in accordance with one or more embodiments of the invention, the design of various components of the dry powder inhalation device can be defined to accommodate different inspiratory flow rates and achieve certain airflow properties including, for example and without limitation, the length and or cross sectional profile of the inhalation tube, the diameter of the extension as well as the diameter or configuration of the impeller (e.g., the size, spacing and angle of the blades and size of the openings between blades).

Figure 19A:
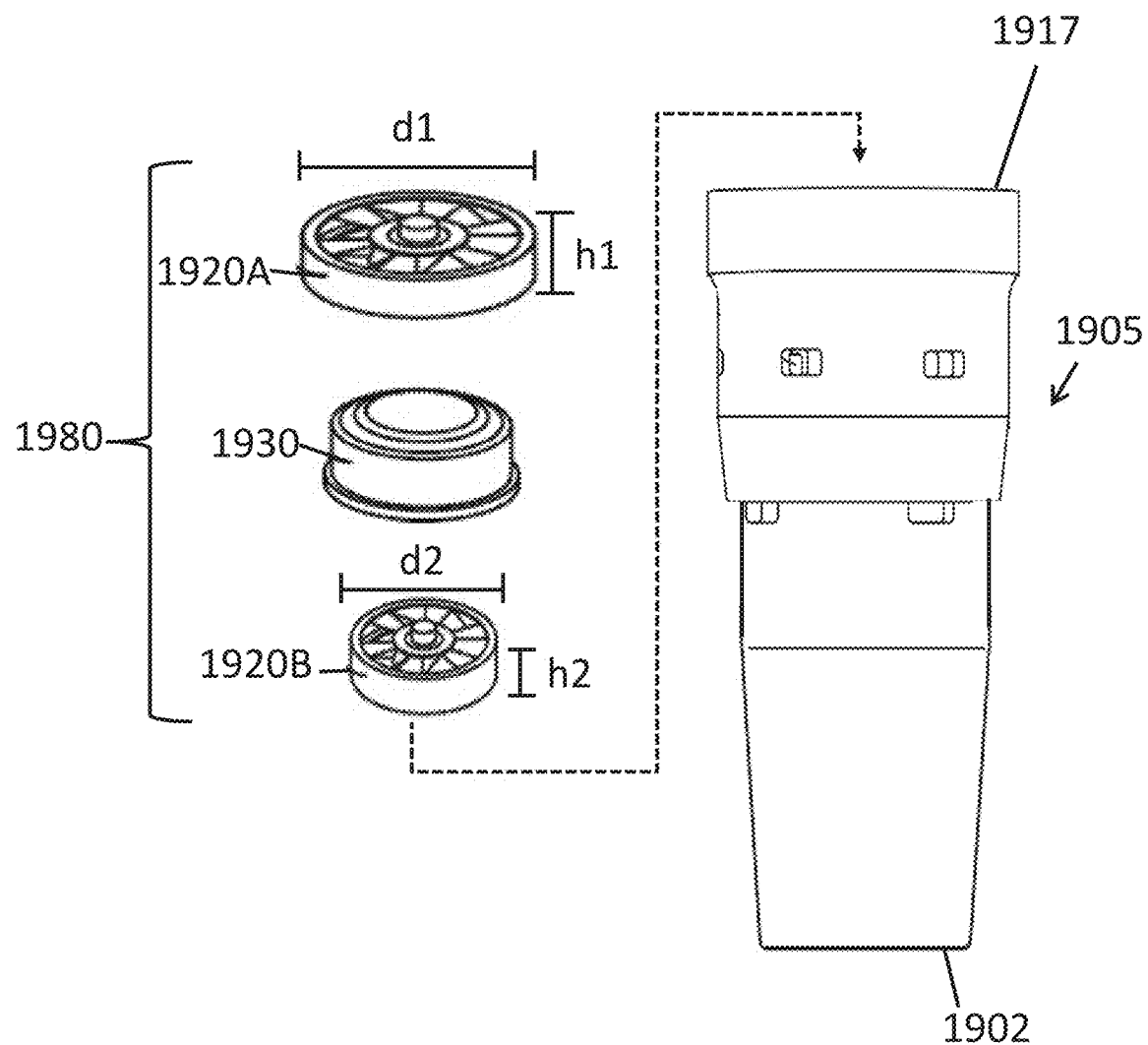
FIG. 19A provides a side view of an exploded dry powder inhaler in accordance with some embodiments of the present invention.

For instance, FIG. 19A is an exploded side view of an exemplary dry powder inhaler 1900. As shown the inhaler device 1900 includes tube-like inhaler body 1905 having a narrowing diameter as it extends between a wider second end 1917 to a narrower first end 1902. When a negative pressure is applied to the first end, the narrowing cross-sectional profile of the inhaler body can facilitate the delivery of dry powder medication, for example and without limitation, by causing the speed of the air flowing longitudinally toward the first end to increase as it nears the first end.

Like the exemplary inhaler device described in connection with FIG. 18A, the inhaler body 1905 can also be configured to receive an assembly 1980 of components within its interior volume. In particular, the assembly 1980 includes two impellers 1920A and 1920B disposed on opposite sides of a dry powder container 1930. Although not shown, it should be appreciated that one or more puncturing devices can be included in the assembly so as to facilitate opening of the container on one or more sides thereof to release powder contained therein during use. Similarly, although not shown in FIG. 19A, it should also be understood that the dry powder inhaler 1900 can include one or more mounts configured to support and locate one or more of the impellers 1920A and 1920B as well as other components of the assembly 1980 that are provided within the inhaler body 1905.

FIG. 19A further illustrates that the impellers 1920A and 1920B have a respective diameters, d1 and d2, which can be different and, as a result, the two impellers should have different air-flow properties. Similarly, the blades of impellers 1920A and 1920B can have different heights, namely, h1 and h2, respectively. As can be appreciated, impeller 1920A having blades with height h1, and impeller 1920B having blades with height h2 further contributes to the two impellers having different respective airflow properties. In addition to height and diameter, other impeller features that can be defined to adjust the flow rates and airflow properties across the impeller can include, for example and without limitation, the size, spacing and angle of the blades and size of the openings between blades.

Although the impellers are shown and described as having a circumferential ring that surrounds the blades and openings, a variety of impeller and/or propeller designs can be implemented to assist the flow of air and dry powder through the interior volume of the inhalation device during use. For instance, in some implementations, one or more of the impellers can be replaced with propellers having blades that are not bounded by a circumferential ring. Moreover, as noted above, the impellers or propellers can be configured to facilitate the pushing of air into the perforated dry powder container and/or draw air from the container during use.

In addition, where multiple impellers are used, the impellers can be configured to facilitate respective air flow characteristics. For instance, an impeller positioned proximate to the underside of the dry powder container, say, impeller 1620A of dry powder inhaler 1600 shown in FIG. 16A, can be configured to create turbulence in the space between the impeller and the underside of the dry powder container (e.g., container 1630) so as to aerosolize the dry powder, while also being configured to direct the aerosolized powder and air toward the first end of the inhaler device 1600. By way of further example, other impellers, say, impeller 1620B of inhaler device 1600, can be configured to primarily direct air and powder axially through the interior volume of the inhaler body toward the end that the user is drawing air from (e.g., first end 1602). In this manner, the exemplary multi-impeller systems can assist in evacuation of powder from the container and moving the evacuated medication and air toward the first end for inhalation by the user.

Figure 19B:
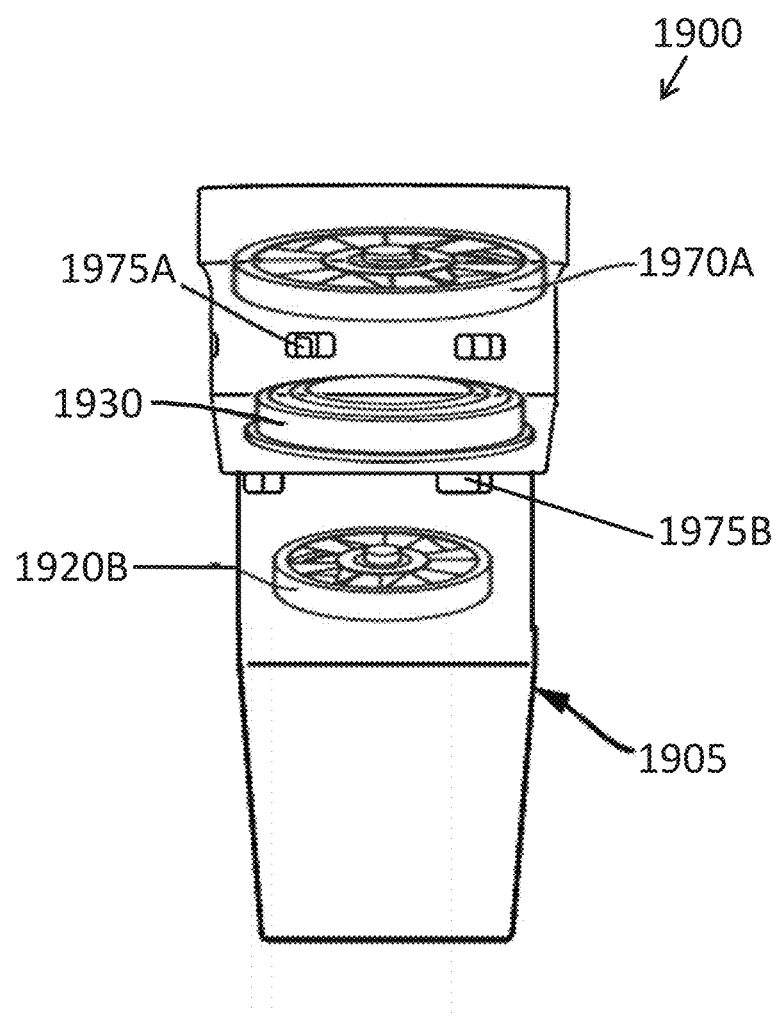
FIG. 19B provides a simplified side view of an assembled dry powder inhaler in accordance with some embodiments of the present invention.

Although not expressly discussed in connection with FIGS. 16A-19A, it should be appreciated that, in some embodiments, the sidewall of the exemplary inhaler device bodies can include one or more openings that extend through the thickness of the sidewall and serve to facilitate air flow through various sections of the internal volume of the inhaler device and through the components of the assembly provided therein. For instance, FIG. 19B depicts the dry powder inhalation device 1900 with the components of the assembly provided at respective heights within the internal volume of the inhaler body 1905 and further depicts openings that facilitate air flow from outside of the extension into corresponding regions of the interior volume of the inhaler body.

As noted, the openings can be located at various levels along the inhaler body so as to facilitate the flow of air into the corresponding regions of the interior volume and through one or more components of the assembly toward the first end 1902 when in use. For instance, as shown in FIG. 19B, preferably, one or more lower side openings 1975B can be provided through the side wall of the inhaler body at a level that is below the dry powder container 1930 and above the bottom-most impeller 1920B that is housed within the body towards the first (e.g. bottom) end 1902. Accordingly, in the inflow of air through lower side openings can facilitate the evacuation of dry powder from the dry powder container and can facilitate the flow of air and/or dry powder through the impeller 1920B toward the first end 1902. In addition, an upper side opening 1975A can also be provided at a level that is above the dry powder container and the top-most impeller 1920A that is housed within body towards the second (e.g., top) end 1917. Accordingly, in the inflow of air through upper side openings into the interior volume of the body can facilitate the pushing of air by the impeller 1920A into the dry powder container and toward the second impeller 1920B and first end 1902. It should be understood that any number of air holes can be provided at a given level and that air holes can be provided at any number of different levels along the inhaler body. More specifically, openings can be provided above and/or below one or more of the components of the assembly contained within the inhaler body. For example and without limitation, air holes can be provided above the dry powder container to facilitate airflow into a top side of the container and out the bottom side thereof, and openings can be provided below the container to facilitate transportation of the dry powder toward the mouthpiece of the inhaler device. In addition, in some instances, air holes can be provided at the same level as one or more of the assembly components, say, at the same level as the dry powder container so as to facilitate airflow into the container through sides thereof.

When in use, dry powder inhalers 100, 700, 1200, 1600, 1700, 1800, 1900, and/or any variants thereof as disclosed herein may be able to deliver a maximum amount of dry powder or dry particles in a single inhalation, which is related to the capacity of the dry powder container 130, 1630, 1730, 1830, and/or 1930, (e.g. size 000, 00, OE, 0, 1, 2, 3, and 4, with respective volumetric capacities of 1.37 ml, 950 µl, 770 µl, 680 µl, 480 µl, 360 µl, 270 µl, and 200 µl). Accordingly, delivery of a desired dose or effective amount may require two or more inhalations. Preferably, each dose that is administered to a subject in need thereof contains an effective amount of respirable dry particles or dry powder and is administered using no more than about 4 inhalations. For example, each dose of respirable dry particles or dry powder can be administered in a single inhalation or 2, 3, or 4 inhalations. The respirable dry particles and dry powders are preferably administered in a single, breath-activated step using dry powder inhalers 100, 700, 1200, 1600, 1700, 1800, 1900, and/or any variants thereof as disclosed herein. When this type of device is used, the energy of the subject's inhalation both disperses the respirable dry particles and draws them into the respiratory tract.

Figure 15:
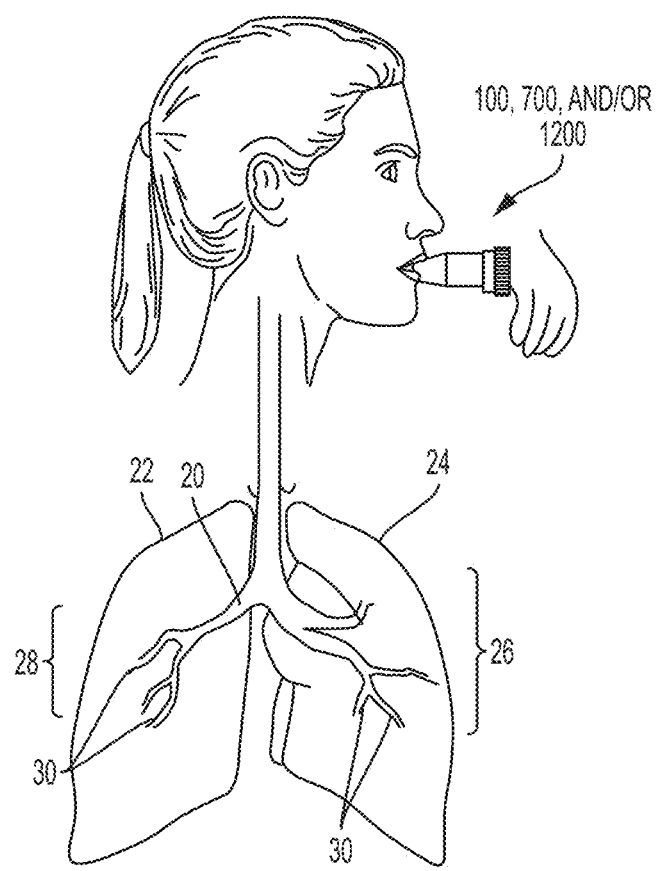
FIG. 15 is a schematic view of a patient using a dry powder inhaler in accordance with some embodiments of the present invention.

Referring to FIG. 15, in a dry powder inhalation technique, a patient can use a dry powder inhaler 100, 700, 1200, 1600, 1700, 1800, 1900, and/or any variants thereof as disclosed herein to inhale a dry powder formulation of a drug, such as a NSAID. The dose is effective to reduce a risk of a thromboembolic event in the patient. The lung is an efficient filter, and generally only permits entry of particles having a size of less than 5 μm. Here, after the drug enters the main stem bronchus, the drug will enter each lung. The drug can then pass through the bronchial trees until reaching the individual alveoli in the lungs. Thus, the dry powder inhaler 100, 700, 1200, 1600, 1700, 1800, 1900, and/or any variants thereof as disclosed herein can allow the patient to self-administer a dosage of particles having a size of from about 1 μm and about 5 μm; alternatively, the particle size can be from about 2 μm to about 4 μm.

In some instances, blades 310 of impeller 120, 1620A, 1620B, 1720A, 1720B, 1820A, 1820B, 1920A and/or 1920B may have a sharp edge and, in these instances, blades 310 may serve to cut or otherwise break up (as may be the case with clumping of the dry powder) or otherwise alter dry powder as it flows through impeller 120, 1620A, 1620B, 1720A, 1720B, 1820A, 1820B, 1920A and/or 1920B. Additionally, or alternatively, surfaces of impeller 120, 1620A, 1620B, 1720A, 1720B, 1820A, 1820B, 1920A and/or 1920B, puncturing device 125, 1625, 1725A, and/or 1725B, interior surfaces of extension 115, and/or 1615 and/or interior surfaces of inhalation tube 110, 715, 1205, 1605, 1705, and/or 1805 may be manufactured so that they have a surface with a low coefficient of friction that prohibits attachment of the dry powder thereto. For example, these surfaces may be may be manufactured so as to have a very smooth surface and/or may be coated with a material (e.g., polytetrafluoroethylene (PTFE)) to inhibit attachment of the dry powder thereto.

The dry powder inhaler(s) 100, 700, 1200, 1600, 1700, 1800, 1900, and/or any variants thereof as disclosed herein disclosed herein may be designed for a one-time/disposable use or repetitive uses. When designed for repetitive use, a user may disassemble dry powder inhaler(s) 100, 700, 1200, 1600, 1700, 1800, 1900, and/or any variants thereof as disclosed herein in order to, for example, clean or replace one or more components thereof.

Exemplary Methods of use for Dry Powder Inhaler

As discussed above, an assembly of impeller 120, 1620A, 1620B, 1720A, 1720B, 1820A, 1820B, 1920A, and/or 1920B, puncturing device 125, 1625, 1725A, and/or 1725B, and dry powder container 130, 1630, 1730, 1830, and/or 1930, may reside within extension 115 and may be held in place within extension 115 by cap 135, and/or 1635 and/or cover 705. This assembly may be the static, or unused state, of dry powder inhaler(s) 100, 700, 1200, 1600, 1700, 1800, 1900, and/or any variants thereof as disclosed herein. In this way, the assembled dry powder inhaler(s) 100, 700, 1200, 1600, 1700, 1800, 1900, and/or any variants thereof as disclosed herein may be portable or otherwise easily carried by a user and/or a healthcare provider. In many instances, dry powder inhaler(s) 100, 700, 1200, 1600, 1700, 1800, 1900, and/or any variants thereof as disclosed herein may be provided with the assembly of impeller 120, 1620A, 1620B, 1720A, 1720B, 1820A, 1820B, 1920A, and/or 1920B, puncturing device 125, 1625, 1725A, and/or 1725B, and dry powder container 130, 1630, 1730, 1830, and/or 1930 already positioned within extension 115. In other instances, a user may be required to assemble one or more components of dry powder inhaler(s) 100, 700, 1200, 1600, 1700, 1800, 1900, and/or any variants thereof as disclosed herein prior to use.

When release of the dry powder residing in the dry powder container 130, 1630, 1730, 1830, and/or 1930 is desired, a user and/or patient (in the case where a doctor, or other healthcare provider that is administering the dry powder to the patient) may remove cap 135, and/or 1635 and press dry powder container 130, 1630, 1730, 1830, and/or 1930 onto puncturing device 125, 1625, 1725A, and/or 1725B thereby puncturing lid 510 so as to enable the dry powder to be released from dry powder container 130, 1630, 1730, 1830, and/or 1930. Once released, the dry powder may pass through impeller 120, 1620A, 1620B, 1720A, 1720B, 1820A, 1820B, 1920A, and/or 1920B so that it may be drawn into the lungs of the user and/or patient by way of inhalation tube 110, 715, 1205, 1605, 1705, and/or 1805.

In some embodiments, a user inhaling (or otherwise creating a negative pressure) may cause impeller 120, 1620A, 1620B, 1720A, 1720B, 1820A, 1820B, 1920A, and/or 1920B to rotate and consequently cause a negative pressure, or wind tunnel effect, in the interior of inhalation tube 115 that may serve to assist in the evacuation of dry powder from dry powder container 130, 1630, 1730, 1830, and/or 1930 through the interior volume of the extension and into the interior of the inhalation tube 110, 715, 1205, 1605, 1705, and/or 1805 so that the dry powder may be inhaled by the user and/or patient. In some implementations, impeller 120, 1620A, 1620B, 1720A, 1720B, 1820A, 1820B, 1920A, and/or 1920B can also be configured to provide feedback to the user and/or patient that it is rotating by producing a noise like a whistle or whirring noise.

In some implementations, dry powder inhaler(s) 100, 700, 1200, 1600, 1700, 1800, 1900, and/or any variants thereof as disclosed herein and the individual components can be designed, or modified, to accommodate individuals with impaired breathing or with poor rate of inhalation. For example, dry powder inhaler(s) 100, 700, 1200, 1600, 1700, 1800, 1900, and/or any variants thereof as disclosed herein can be designed to work with an inspiratory flow rate of, for example, 40-80 liters per minute. Exemplary design elements of the dry powder inhaler that can be adjusted to accommodate different inspiratory flow rates can include, for example and without limitation, the length and or cross sectional profile of the inhalation tube, the diameter of the extension as well as the diameter or configuration of the impeller (e.g., the size, spacing and angle of the blades and size of the openings between blades). Additional design elements that can be adjusted to achieve certain airflow and dry powder delivery properties can include the size of any combination of the openings and orifices that are provided in the sidewalls or bottom of the extension as well as the openings provided in individual components that comprise the assembly contained within the extension. Varying the size, number and spacing of the extensions or blades that puncture the bottom lid of the dry powder container can also serve to adjust the ease with which the dry powder can be evacuated from the interior of the dry powder container and passed through the dry powder inhalation device.

Although the medication substance is referred to as a dry powder contained within a container that is generally shown and described as having a cup portion and a lid or cover that define a sealed container having a generally flat and wide top and bottom surface and relatively shorter sidewalls, the configuration of the container is not intended to be so limited. The powdered or aerosolized respirable dry powder medication can be contained within containers having any number of different sizes, shapes, configurations, and constructions; for instance, a puck-shaped container, a capsule, a cartridge, a packet, and the like without departing from the scope of the disclosed invention.

Dry Powders

The subject technology relates to respirable dry powders and dry particles that comprise an NSAID, such as ASA, as an active ingredient.

In one aspect, the dry particles of the subject technology are comparatively small, and preferably are dispersible. The size of the dry particles can be expressed in a variety of ways that are conventional in the art, such as, fine particle fraction (FPF), volumetric median geometric diameter (VMGD), or mass median aerodynamic diameter (MMAD).

In one embodiment, the respirable dry particles of the subject technology can have an MMAD of about 5 μm or less, about 0.5 μm to about 5 μm, about 1 μm to about 5 μm, about 4 μm or less (e.g., about 1 μm to about 4 μm), about 3.8 μm or less (e.g. about 1 μm to about 3.8 μm), about 3.5 μm or less (e.g. about 1 μm to about 3.5 μm), about 3.2 μm or less (e.g. about 1 μm to about 3.2 μm), about 3 μm or less (e.g. about 1 μm to about 3.0 μm), about 2.8 μm or less (e.g. about 1 μm to about 2.8 μm), about 2.2 μm or less (e.g. about 1 μm to about 2.2 μm), about 2.0 μm or less (e.g. about 1 μm to about 2.0 μm) or about 1.8 μm or less (e.g. about 1 micron to about 1.8 μm).

Alternatively or in addition, the dry powders and dry particles of the subject technology have a FPF of the total dose of less than 5.0 μm (FPF_TD<5.0 μm) of at least about 20%, at least about 30%, at least about 45%, preferably at least about 40%, at least about 45%, at least about 50%, at least about 60%, at least about 65% or at least about 70%. Alternatively or in addition, the dry powders and dry particles of the subject technology have a FPF of the emitted dose of less than 5.0 μm (FPF_ED<5.0 μm) of at least about 45%, preferably at least about 50%, at least about 60%, at least about 65%, at least about 70%, at least about 75%, at least about 80%, or at least about 85%.

D10 represents the particle diameter corresponding to 10% cumulative (from 0 to 100%) undersize particle size distribution. In other words, if D10 is A um, we can say 10% of the particles in the tested sample are smaller than A micrometers, or the percentage of particles smaller than A micrometer is 10%. D50 represents the particle diameter corresponding to 50% cumulative undersize particle size distribution. D90 represents the particle diameter corresponding to 90% cumulative undersize particle size distribution. As used herein, D10 and D(v0.1) are interchangeable; D50 and D(v0.5) are interchangeable; D90 and D(v0.9) are interchangeable.

In one embodiment, the respirable dry powders and dry particles of the subject technology can have a water or solvent content of less than about 15% by weight of the respirable dry particle. For example, the respirable dry particles of the subject technology can have a water or solvent content of less than about 15% by weight, less than about 13% by weight, less than about 11.5% by weight, less than about 10% by weight, less than about 9% by weight, less than about 8% by weight, less than about 7% by weight, less than about 6% by weight, less than about 5% by weight, less than about 4% by weight, less than about 3% by weight, less than about 2% by weight, less than about 1% by weight or be anhydrous. The respirable dry particles of the subject technology can have a water or solvent content of less than about 6% and greater than about 1%, less than about 5.5% and greater than about 1.5%, less than about 5% and greater than about 2%, about 2%, about 2.5%, about 3%, about 3.5%, about 4%, about 4.5% about 5%.

Depending on the specific applications of the dry powders described herein, the dry powder and particles may contain a varying percentage of active ingredient in the composition. For example, the dry particles may contain 3% or more, 5% or more, 10% or more, 15% or more, 20% or more, 25% or more, 30% or more, 35% or more, 40% or more, 50% or more, 60% or more, 70% or more, 75% or more, 80% or more, 85% or more, 90% or more, or 95% or more (weight percentage) of the active ingredient (e.g., ASA).

Delivery and Treatment with Dry Powders

According to some embodiments disclosed herein, absorption of NSAIDs administered by DPI or MDI through the pulmonary capillaries and epithelium may provide an immediately effective treatment to address symptoms of thromboembolic events.

In accordance with some embodiments, the dry powder administration of the NSAID, such as a salicylate like ASA, can be highly porous and demonstrate a sponge-like morphology or be a component of a carrier particle. The particles can also demonstrate a spheroidal shape, by which the shape and porous surface can serve to decrease the area of contact between particles, thereby leading to less particle agglomeration and more effective distribution throughout the lung. Dry powder technologies, such as PulmoSphere®, may be implemented in embodiments of the methods and systems disclosed herein.

The absolute geometric diameter of the particles measured at 1 bar using the HELOS system is not critical provided that the particle's envelope density is sufficient such that the MMAD is in one of the ranges listed herein, wherein MMAD is VMGD times the square root of the envelope density (MMAD=VMGD*sqrt (envelope density)). If it is desired to deliver a high unit dose of salt using a fixed volume-dosing container, then, particles of higher envelop density are desired. High envelope density allows for more mass of powder to be contained within the fixed volume-dosing container. Envelope densities may be greater than 0.1 g/cm$^3$, greater than 0.25 g/cm$^3$, greater than 0.4 g/cm$^3$, greater than 0.5 g/cm$^3$, and greater than 0.6 g/cm$^3$.

The respirable dry powders and particles of the subject technology can be employed in compositions suitable for drug delivery via the respiratory system. For example, such compositions can include blends of the respirable dry particles of the subject technology and one or more other dry particles or powders, such as dry particles or powders that contain another active agent, or that consist of or consist essentially of one or more pharmaceutically acceptable excipients.

Respirable dry powders and dry particles suitable for use in the methods of the subject technology can travel through the upper airways (i.e., the oropharynx and larynx), the lower airways, which include the trachea followed by bifurcations into the bronchi and bronchioli, and through the terminal bronchioli which in turn divide into respiratory bronchiole leading then to the ultimate respiratory zone, the alveoli or the deep lung. In one embodiment of the subject technology, most of the mass of respirable dry powders or particles deposit in the deep lung. In another embodiment of the subject technology, delivery is primarily to the central airways. In another embodiment, delivery is to the upper airways.

The respirable dry particles or dry powders of the subject technology can be delivered by inhalation at various parts of the breathing cycle (e.g., laminar flow at mid-breath). An advantage of the high dispersibility of the dry powders and dry particles of the subject technology is the ability to target deposition in the respiratory tract. For example, breath controlled delivery of nebulized solutions is a recent development in liquid aerosol delivery (Dalby et al. in *Inhalation Aerosols*, edited by Hickey 2007, p. 437). In this case, nebulized droplets are released only during certain portions of the breathing cycle. For deep lung delivery, droplets are released in the beginning of the inhalation cycle, while for central airway deposition, they are released later in the inhalation.

The dry powders of this subject technology provide advantages for targeting the timing of drug delivery in the breathing cycle and also specific location in the human lung. Because the respirable dry powders of the subject technology can be dispersed rapidly, such as within a fraction of a typical inhalation maneuver, the timing of the powder dispersal can be controlled to deliver an aerosol at specific times within the inhalation.

With a highly dispersible powder, the complete dose of aerosol can be dispersed at the beginning portion of the inhalation. While the patient's inhalation flow rate ramps up to the peak inspiratory flow rate, a highly dispersible powder will begin to disperse already at the beginning of the ramp up and could completely disperse a dose in the first portion of the inhalation. Since the air that is inhaled at the beginning of the inhalation will ventilate deepest into the lungs, dispersing the most aerosol into the first part of the inhalation is preferable for deep lung deposition. Similarly, for central deposition, dispersing the aerosol at a high concentration into the air which will ventilate the central airways can be achieved by rapid dispersion of the dose near the mid to end of the inhalation. This can be accomplished by a number of mechanical and other means such as a switch operated by time, pressure or flow rate that diverts the patient's inhaled air to the powder to be dispersed only after the switch conditions are met.

Suitable intervals between doses that provide the desired therapeutic effect can be determined based on the severity of the condition, overall well-being of the subject and the subject's tolerance to respirable dry particles and dry powders as well as other considerations. Based on these and other considerations, a clinician can determine appropriate intervals between doses. Generally, respirable dry particles and dry powders are administered once, twice or three times a day, as needed.

In some embodiments the amount of NSAID delivered to the respiratory tract (e.g., lungs, respiratory airway) is about 0.001 mg/kg body weight/dose to about 2 mg/kg body weight/dose, about 0.002 mg/kg body weight/dose to about 2 mg/kg body weight/dose, about 0.005 mg/kg body weight/dose to about 2 mg/kg body weight/dose, about 0.01 mg/kg body weight/dose to about 2 mg/kg body weight/dose, about 0.02 mg/kg body weight/dose to about 2 mg/kg body weight/dose, about 0.05 mg/kg body weight/dose to about 2 mg/kg body weight/dose, about 0.075 mg/kg body weight/dose to about 2 mg/kg body weight/dose, about 0.1 mg/kg body weight/dose to about 2 mg/kg body weight/dose, about 0.2 mg/kg body weight/dose to about 2 mg/kg body weight/dose, about 0.5 mg/kg body weight/dose to about 2 mg/kg body weight/dose, or about 0.75 mg/kg body weight/dose to about 2 mg/kg body weight/dose.

In certain embodiments, at least about 50%, at least about 60%, at least about 70%, at least about 75%, at least about 80%, at least about 85%, at least about 90%, at least about 95%, or at least about 99%, of the administered ASA reaches the systemic circulation of a subject within about 60 minutes upon administration, or within about 40 minutes upon administration, or within about 30 minutes upon administration, or within about 20 minutes upon administration, or within about 15 minutes upon administration, or within about 5 minutes upon administration.

In certain embodiments, the method and delivery devices described herein can deliver ASA, and pharmacologically active metabolic byproducts of ASA thereof, to the systemic circulation, at levels that are substantially the same, or higher as compared to those delivered by oral administration of about 30-160 mg of ASA, specifically, 40 mg, 50 mg, 60 mg, 80 mg or 160 mg.

The doses of ASA administered in order to achieve a level (or an average level among a population of patients) that is substantially the same, or higher as compared to those delivered by oral administration of about 30 mg, about 40 mg, about 50 mg, about 80 mg, or about 160 mg of ASA can be determined by conventional methods. The dosing, administration techniques and schedules are known in the art and are within the ability of the skilled clinician. For example, the serum level of ASA, or a metabolite thereof, in a subject (or average serum level among a population of subjects) can be determined by conventional pharmacokinetic or pharmacodynamics studies.

In certain embodiments, the method and delivery devices described herein can deliver ASA to the systemic circulation such that the circulating plasma level of ASA is at least about 1 µg/mL, at least about 2 µg/mL, at least about 3 µg/mL, at least about 4 µg/mL, at least about 5 µg/mL, or at least about 6 µg/mL, about 7 µg/mL, about 8 µg/mL, about 9 µg/mL, about 10 µg/mL, about 11 µg/mL, about 12 µg/mL or about 15 µg/mL within about 60 minutes upon administration, or within about 40 minutes upon administration, or within about 30 minutes upon administration, or within about 20 minutes upon administration, or within about 15 minutes upon administration, or within about 5 minutes upon administration.

If desired or indicated, the respirable dry particles and dry powders described herein can be administered with one or more other therapeutic agents. The other therapeutic agents can be administered by any suitable route, such as orally, parenterally (e.g., intravenous, intraarterial, intramuscular, or subcutaneous injection), topically, by inhalation (e.g., intrabronchial, intranasal or oral inhalation, intranasal drops), rectally, vaginally, and the like. The respirable dry particles and dry powders can be administered before, substantially concurrently with, or subsequent to administration of the other therapeutic agent. Preferably, the respirable dry particles and dry powders and the other therapeutic agent are administered so as to provide substantial overlap of their pharmacologic activities.

The compositions and methods of the present disclosure provide for a method for treating (including prophylactic treatment or reducing the risk) of a cardiovascular disease (such as thrombosis), comprising administering to the respiratory tract of a subject in need thereof an effective amount of respirable dry particles or dry powder, as described herein.

Cardiovascular diseases include, for example, atherosclerosis, coronary artery disease (CAD), angina pectoris (commonly known as "angina"), thrombosis, ischemic heart disease, coronary insufficiency, peripheral vascular disease, myocardial infarction, cerebrovascular disease (such as stroke), transient ischemic attack, arteriolosclerosis, small vessel disease, elevated cholesterol, intermittent claudication or hypertension.

Methods for Preparing Dry Powders and Dry Particles

The respirable dry particles and dry powders can be prepared using any suitable method. Many suitable methods for preparing respirable dry powders and particles are conventional in the art, and include single and double emulsion solvent evaporation, spray drying, milling (e.g., jet milling), blending, solvent extraction, solvent evaporation, phase separation, simple and complex coacervation, interfacial polymerization, suitable methods that involve the use of supercritical carbon dioxide ($CO_2$), and other suitable methods. Respirable dry particles can be made using methods for making microspheres or microcapsules known in the art. These methods can be employed under conditions that result in the formation of respirable dry particles with desired aerodynamic properties (e.g., aerodynamic diameter and geometric diameter). If desired, respirable dry particles with desired properties, such as size and density, can be selected using suitable methods, such as sieving.

Spray Drying

Inhalable dry particles can be produced by spray drying. Suitable spray drying techniques are described, for example, by K. Masters in "Spray Drying Handbook", John Wiley & Sons, New York (1984); and spray drying techniques developed by BUCHI Laboratory Equipment or GEA Niro drying technology. Generally, during spray drying, heat from a hot gas such as heated air or nitrogen is used to evaporate a solvent from droplets formed by atomizing a continuous liquid feed. If desired, the spray drying or other instruments, e.g., jet milling instrument, used to prepare the dry particles can include an inline geometric particle sizer that determines a geometric diameter of the respirable dry particles as they are being produced, and/or an inline aerodynamic particle sizer that determines the aerodynamic diameter of the respirable dry particles as they are being produced.

For spray drying, solutions, emulsions or suspensions that contain the components of the dry particles to be produced in a suitable solvent (e.g., aqueous solvent, organic solvent, aqueous-organic mixture or emulsion) are distributed to a drying vessel via an atomization device. For example, a nozzle or a rotary atomizer may be used to distribute the solution or suspension to the drying vessel. For example, a rotary atomizer having a 4- or 24-vaned wheel may be used. Examples of suitable spray dryers that can be outfitted with either a rotary atomizer or a nozzle, include, Mobile Minor Spray Dryer or the Model PSD-1, both manufactured by Niro, Inc. (Denmark). Actual spray drying conditions will vary depending, in part, on the composition of the spray drying solution or suspension and material flow rates. The person of ordinary skill will be able to determine appropriate conditions based on the compositions of the solution, emulsion or suspension to be spray dried, the desired particle properties and other factors. In general, the inlet temperature to the spray dryer is about 100° C. to about 300° C., and preferably is about 220° C. to about 285° C. The spray dryer outlet temperature will vary depending upon such factors as the feed temperature and the properties of the materials being dried. Generally, the outlet temperature is about 50° C. to about 150° C., preferably about 90° C. to about 120° C., or about 98° C. to about 108° C. If desired, the respirable dry particles that are produced can be fractionated by volumetric size, for example, using a sieve, or fractioned by aerodynamic size, for example, using a cyclone, and/or further separated according to density using techniques known to those of skill in the art.

To prepare the respirable dry particles of the subject technology, generally, a solution, emulsion or suspension that contains the desired components of the dry powder (i.e., a feed stock) is prepared and spray dried under suitable conditions. Preferably, the dissolved or suspended solids concentration in the feed stock is at least about 1 g/L, at least about 2 g/L, at least about 5 g/L, at least about 10 g/L, at least about 15 g/L, at least about 20 g/L, at least about 30 g/L, at least about 40 g/L, at least about 50 g/L, at least about 60 g/L, at least about 70 g/L, at least about 80 g/L, at least about 90 g/L, or at least about 100 g/L. The feedstock can be provided by preparing a single solution or suspension by dissolving or suspending suitable components (e.g., salts, excipients, other active ingredients) in a suitable solvent. The solvent, emulsion or suspension can be prepared using any suitable methods, such as bulk mixing of dry and/or liquid components or static mixing of liquid components to form a combination. For example, a hydrophilic component (e.g., an aqueous solution) and a hydrophobic component (e.g., an organic solution) can be combined using a static mixer to form a combination. The combination can then be atomized to produce droplets, which are dried to form respirable dry particles. Preferably, the atomizing step is performed immediately after the components are combined in the static mixer.

In one embodiment, respirable dry particles that comprise ASA can be prepared by spray drying. Spray drying is a commonly used method of drying a liquid feed through a hot gas. It is a method whereby solutions or slurries can be rapidly dried to particulate form by atomizing the liquid in a heated chamber. Typically, the hot gas can be air although when preparing chemically sensitive materials such as pharmaceuticals, and where solvents such as ethanol are used, and oxygen-free atmosphere is required and so nitrogen task will typically be used. Spray drying is frequently used in the food preparation industry and has become an important method for the dehydration of fluid foods such as milk, coffee, and egg powder. The process is also adaptable to preparations of pharmaceutical and chemical formulations.

The liquid feed varies depending on the material being dried and is not limited to food or pharmaceutical products, and may be a solution, colloid or suspension. The process is a one-step rapid method that typically eliminates additional processing. By controlling process conditions particles of the desired size can be reproducibly formed. In some cases, excipients can be included with the active pharmaceutical ingredient such that a complex particle of API and excipient can be produced in a single step process. In other cases, an active pharmaceutical particulate preparation can be produced in a first spray-drying process, and that product then modified by the subsequent addition of one or more pharmaceutically acceptable excipients. In some cases it is possible to add excipients by a subsequent spray-drying process.

In some spray-drying methods the liquid feed is pumped through an atomizer nozzle, or array of nozzles, that produce fine droplets that are introduced into the main drying chamber. Atomizers can vary there being rotary, single fluid, two-fluid, and ultrasonic designs. These different designs provide a variety of advantages, applicability and disadvantages depending on the particular spray drying process required. The hot drying gas can be passed as a concurrent or counter-current flow to the atomizer direction. The concurrent flow enables the particles to have a lower residence time within the system and the particle separator thus operates more efficiently. In some systems the particle separator is a cyclone device. The counter-current flow method enables a greater residence time of the particles in the chamber. Therefore, in general a spray-drying method will consist of the steps of pre-concentration of liquid, atomization, drying in a hot gas atmosphere, separation of the dried powder from moist gas, cooling, and then packaging of the finished product.

In one embodiment of the present disclosure, feed solutions with aspirin concentrations of either 2% w/w, or 5% w/w, were prepared by adding aspirin to the appropriate solvent followed by stirring until a homogeneous solution was obtained. A BUCHI spray dryer model B-290 Advanced was used in all experiments. The unit was equipped with a two fluid nozzle. The high-performance cyclones were used to collect the dried product. The spray-drying unit was operated in open cycle, with the aspirator blowing nitrogen at 100% of capacity, corresponding to a flow rate of the dry nitrogen of approximately 40 kg per hour. The flow rate of atomization nitrogen was adjusted to 40 mm or 50 mm in the rotameter, depending on the particular trial. Before feeding the stock solution, the spray dryer was stabilized the solvent. During the stabilization period, the solvent flow rate was adjusted in order to give the target outlet temperature. After stabilization of the outlet temperature, the feed of the spray dryer was commuted from the solvent to the product solution (inlet temperature was then readjusted to maintain the outlet temperature in the target value). At the end of the stock solution, the feed was once more commuted to solvent, in order to rinse the feed line and carry out a controlled shutdown.

Respirable particles can also be produced by jet-milling. See, e.g., techniques developed by Apex Process Technology or Jetpharma SA. Jet milling is a process of using highly compressed air or other gasses, usually in a vortex motion, to impact fine particles against each other in a chamber. Jet mills are capable of reducing solids to particle sizes in the low-micron to submicron range. The grinding energy is created by gas streams from horizontal grinding air nozzles. Particles in the fluidized bed created by the gas streams are accelerated towards the center of the mill, colliding with slower moving particles. The gas streams and the particles carried in them create a violent turbulence and as the particles collide with one another they are pulverized.

Wet polishing is a process that combines a technology to attain a small particle size (either a bottom up technique such as controlled crystallization or nanocrystallization or top down technique such as high shear mixing or high pressure homogenization) with a suitable isolation technology (for example spray drying or filtration with a drying process). These combinations can be used to tune the particle size and morphology to meet specific drug delivery needs. The method allows control of particle size distribution with tight spans and in-process sampling, and maintains crystalline state (little or no amorphous content).

Excipients

Particles described herein can be encapsulated, e.g., by a pharmaceutical excipient such as lactose, sugar, or a polymer.

In addition, particles described herein can be mixed and/or coated with various pharmaceutically acceptable excipients. Excipients can be included in order to improve aerodynamic performance of the active drug, to improve bioavailability, increase stability, to modulate pH, to provide sustained release properties, to provide taste-masking of an irritating drug and/or to improve pharmacokinetic performance.

With dry powder formulations, excipients can also provide a carrier function to reduce clumping of the active pharmaceutical ingredient and to improve suspension of the formulation in the airflow as the pharmaceutical preparation is being inhaled. Such carriers can include substances such as, but not limited to, sugars/sugar alcohols such as glucose, saccharose, lactose and fructose, starches or starch derivatives, oligosaccharides such as dextrins, cyclodextrins and their derivatives, polyvinylpyrrolidine, alginic acid, tylose, silicic acid, cellulose, cellulose derivatives, sugar alcohols such as mannitol or sorbitol, calcium carbonate, calcium phosphate, lactose, lactitol, dextrates, dextrose, maltodextrin, saccharides including monosaccharides, disaccharides, polysaccharides; sugar alcohols such as arabinose, ribose, mannose, sucrose, trehelose, maltose and dextran.

In some cases, an excipient can be provided in order to coat the active pharmaceutical ingredient, thus "masking" it. Masking is especially useful when the unmodified active pharmaceutical is irritating or otherwise unpleasant to the recipient. For example, in some cases it has been shown that coating a bitter molecule with a hydrogenated oil and surfactant combination is effective to cover the otherwise unpleasant taste of the active ingredient.

Particle Size Analysis

The diameter of the respirable dry particles, for example, their VMGD, can be measured using an electrical zone sensing instrument such as a Multisizer lie, (Coulter Electronic, Luton, Beds, England), or a laser diffraction instrument such as a HELOS system (Sympatec, Princeton, N.J.). Other instruments for measuring particle geometric diameter are well known in the art. The diameter of respirable dry particles in a sample will range depending upon factors such as particle composition and methods of synthesis. The distribution of size of respirable dry particles in a sample can be selected to permit optimal deposition within targeted sites within the respiratory system.

Experimentally, aerodynamic diameter can be determined using time of flight (TOF) measurements. For example, an instrument such as the Model 3225 Aerosizer DSP Particle Size Analyzer (Amherst Process Instrument, Inc., Amherst, Mass.) can be used to measure aerodynamic diameter. The Aerosizer measures the time taken for individual respirable dry particles to pass between two fixed laser beams.

Aerodynamic diameter can also be experimentally determined directly using conventional gravitational settling methods, in which the time required for a sample of respirable dry particles to settle a certain distance is measured. Indirect methods for measuring the mass median aerodynamic diameter include the Andersen Cascade Impactor (ACI) and the multi-stage liquid impinger (MSLI) methods. Another method of measuring the aerodynamic diameter is with a Next Generation Impactor (NGI). The NGI operates on similar principles of inertial impaction as the ACI. The NGI may have multiple stages, e.g., seven stages and can be calibrated at flow rates of 30, 60, and 100 LPM. In contrast to the ACI, for which the impactor stages are stacked, the stages of the NGI are all in one plane. Collection cups are used to collect the particles below each stage of the NGI. U.S. Pat. No. 8,614,255. The methods and instruments for measuring particle aerodynamic diameter are well known in the art.

Fine particle fraction (FPF) can be used as one way to characterize the aerosol performance of a dispersed powder. Fine particle fraction describes the size distribution of airborne respirable dry particles. Gravimetric analysis, using a Cascade impactor, is one method of measuring the size distribution, or fine particle fraction, of airborne respirable dry particles. The ACI is an eight-stage impactor that can separate aerosols into nine distinct fractions based on aerodynamic size. The size cutoffs of each stage are dependent upon the flow rate at which the ACI is operated. The ACI is made up of multiple stages consisting of a series of nozzles (i.e., a jet plate) and an impaction surface (i.e., an impaction disc). At each stage an aerosol stream passes through the nozzles and impinges upon the surface. Respirable dry particles in the aerosol stream with a large enough inertia will impact upon the plate. Smaller respirable dry particles that do not have enough inertia to impact on the plate will remain in the aerosol stream and be carried to the next stage. Each successive stage of the ACI has a higher aerosol velocity in the nozzles so that smaller respirable dry particles can be collected at each successive stage.

If desired, a two-stage collapsed ACI can also be used to measure fine particle fraction. The two-stage collapsed ACI consists of only the top two stages of the eight-stage ACI and allows for the collection of two separate powder fractions. Specifically, a two-stage collapsed ACI is calibrated so that the fraction of powder that is collected on stage one is composed of respirable dry particles that have an aerodynamic diameter of less than 5.6 µm and greater than 3.4 µm. The fraction of powder passing stage one and depositing on a collection filter is thus composed of respirable dry particles having an aerodynamic diameter of less than 3.4 µm. The airflow at such a calibration is approximately 60 L/min. Formulation produced by the methods described herein can be effectively delivered at airflow rates ranging from about 20 L/min to about 60 L/min.

An ACI can be used to approximate the emitted dose, which herein is called gravimetric recovered dose and analytical recovered dose. "Gravimetric recovered dose" is defined as the ratio of the powder weighed on all stage filters of the ACI to the nominal dose. "Analytical recovered dose" is defined as the ratio of the powder recovered from rinsing all stages, all stage filters, and the induction port of the ACI to the nominal dose. The FPF TD (<5.0) is the ratio of the interpolated amount of powder depositing below 5.0 µm on the ACI to the nominal dose. The FPF RD (<5.0) is the ratio of the interpolated amount of powder depositing below 5.0 µm on the ACI to either the gravimetric recovered dose or the analytical recovered dose.

Another way to approximate emitted dose is to determine how much powder leaves its container, e.g. capsule or blister, upon actuation of a dry powder inhaler (DPI). This takes into account the percentage leaving the capsule, but does not take into account any powder depositing on the DPI. The emitted dose is the ratio of the weight of the capsule with the dose before inhaler actuation to the weight of the capsule after inhaler actuation. This measurement can also be called the capsule emitted powder mass (CEPM).

A Multi-Stage Liquid Impinger (MSLI) is another device that can be used to measure particle size distribution or fine particle fraction. The Multi-stage liquid Impinger operates on the same principles as the ACI, although instead of eight stages, MSLI has five. Additionally, each MSLI stage consists of an ethanol-wetted glass frit instead of a solid plate. The wetted stage is used to prevent particle bounce and re-entrainment, which can occur when using the ACI. U.S. Pat. No. 8,614,255.

EXAMPLES

Device 1: A dry powder inhalation device comprising:
  an inhaler body, the inhaler body comprising one or more sidewalls extending between an open first end and an open second end and surrounding an interior volume, at least a portion of the inhaler body being sized and shaped to receive an assembly of components within the interior volume; and
  the assembly of components, wherein the components are arranged in series within the interior volume and include:
    a dry powder container that contains a measured amount of dry powder, wherein one or more walls of the dry powder container are configured to be selectively opened thereby allowing the dry powder to be released from the container into the internal volume of the inhaler body, and
    a plurality of impellers positioned within the internal volume, wherein each of the a plurality of impellers has a top side and an opposing bottom side and includes a series of blades defining openings therebetween and is configured to rotate about a respective central axis, and wherein the a plurality of impellers are configured to direct air and the released dry powder toward the first end.

Device 2: The dry powder inhalation device according to device 1, further comprising:
  one or more puncturing devices configured to selectively open the one or more walls of the dry powder container.

Device 3: The dry powder inhalation device according to device 1, wherein the plurality of impellers are configured to rotate upon application of negative pressure to the first end of the inhaler body by a user inhaling air through the inhaler body from the first end.

Device 4: The dry powder inhalation device according to device 3, wherein the rotation about the respective central axis of one of the plurality of impellers directs the air and the dry powder from above the top side of the impeller axially through the openings and through the internal volume of the inhaler body toward the first end.

Device 5: The dry powder inhalation device according to device 4, wherein the plurality of impellers include a respective central axis pin and are supported within the internal volume by one or more mounts that are configured to receive an end of the respective central axis pin.

Device 6: The dry powder inhalation device according to device 1, wherein one or more of the plurality of impellers are positioned within the interior volume at a level that is below the dry powder container and are configured to draw air and dry powder from the dry powder container through openings provided on a bottom side of the dry powder container.

Device 7: The dry powder inhalation device according to device 1, wherein one or more of the plurality of impellers are positioned within the interior volume at a level that is above the dry powder container and are configured to direct air into the dry powder container through openings provided on at least a top side of the dry powder container.

Device 8: The dry powder inhalation device according to device 1, wherein:
  one or more of the plurality of impellers are positioned within the interior volume at a level that is below the dry powder container and are configured to draw air and dry powder from the dry powder container through openings provided on a bottom side of the dry powder container; and
  one or more of the plurality of impellers are positioned within the interior volume at a level that is above the dry powder container and are configured to direct air into the dry powder container through openings provided on at least a top side of the dry powder container.

Device 9: The dry powder inhalation device according to device 1, wherein the plurality of impellers are joined to define an impeller assembly.

Device 10: The dry powder inhalation device according to device 1, wherein at least two of the plurality of impellers rotate about respective axes in a common rotational direction.

Device 11: The dry powder inhalation device according to device 1, wherein at least two of the plurality of impellers rotate about their respective axes in opposite rotational directions.

Device 12: The dry powder inhalation device according to device 1, wherein at least two of the plurality of impellers have different respective diameters.

Device 13: The dry powder inhalation device according to device 1, wherein at least two of the plurality of impellers have different respective heights.

Device 14: The dry powder inhalation device according to device 1, wherein at least one of the plurality of impellers is configured to achieve different airflow properties within the internal volume from at least one other of the plurality of impellers.

Device 15: The dry powder inhalation device according to device 1, wherein the plurality of impellers are configured to aerosolize the dry powder.

Device 16: The dry powder inhalation device according to device 1, wherein the one or more sidewalls surrounding the interior volume comprise one or more orifices therethrough, wherein the one or more orifices allow airflow through the one or more sidewalls surrounding the interior volume into the interior volume of the inhaler body.

Device 17: The dry powder inhalation device according to device 13, wherein at least one impeller of the assembly is positioned within the interior volume at a level that is between one or more of the orifices and the first end of the inhaler body.

Device 18: The dry powder inhalation device according to device 2, wherein the puncturing device is positioned within the interior volume at a level that is above a top side of an impeller and below the bottom side of the dry powder container.

Device 19: The dry powder inhalation device according to device 1, wherein one or more of the components defining the assembly are positioned within the interior volume independent of the remaining components.

Device 20: A dry powder inhalation device comprising:

an inhaler body, the inhaler body comprising one or more sidewalls extending between an open first end and an open second end and surrounding an interior volume, at least a portion of the inhaler body being sized and shaped to receive an assembly of components within the interior volume; and the assembly of components, wherein the components are arranged in series within the interior volume and include:

a dry powder container that contains a measured amount of dry powder, wherein one or more walls of the dry powder container are configured to be selectively opened thereby allowing the dry powder to be released from the container into the internal volume of the inhaler body, a plurality of puncturing devices configured to selectively open the one or more walls of the dry powder container, and an impeller positioned within the internal volume, wherein the impeller has a top side and an opposing bottom side and includes a series of blades defining openings therebetween and is configured to rotate about a respective central axis, and wherein the impeller is configured to direct air and the released dry powder toward the first end.

Device 21: The dry powder inhalation device according to device 20, comprising a plurality of impellers.

Device 22: The dry powder inhalation device according to device 21, wherein the two or more impellers are configured to rotate upon application of negative pressure to the first end of the inhaler body by a user inhaling air through the inhaler body from the first end.

Device 23: The dry powder inhalation device according to device 22, wherein the rotation about the respective central axis of one of the plurality of impellers directs the air and the dry powder from above the top side of the impeller axially through the openings and through the internal volume of the inhaler body toward the first end.

Device 24: The dry powder inhalation device according to device 22, wherein the plurality of impellers include a respective central axis pin and are supported within the internal volume by one or more mounts that are configured to receive an end of the respective central axis pin.

Device 25: The dry powder inhalation device according to device 21, wherein one or more of the plurality of impellers are positioned within the interior volume at a level that is below the dry powder container and are configured to draw air and dry powder from the dry powder container through openings provided on a bottom side of the dry powder container.

Device 26: The dry powder inhalation device according to device 21, wherein one or more of the plurality of impellers are positioned within the interior volume at a level that is above the dry powder container and are configured to direct air into the dry powder container through openings provided on at least a top side of the dry powder container.

Device 27: The dry powder inhalation device according to device 21, wherein:

one or more of the plurality of impellers are positioned within the interior volume at a level that is below the dry powder container and are configured to draw air and dry powder from the dry powder container through openings provided on a bottom side of the dry powder container; and one or more of the plurality of impellers are positioned within the interior volume at a level that is above the dry powder container and are configured to direct air into the dry powder container through openings provided on at least a top side of the dry powder container.

Device 28: The dry powder inhalation device according to device 21, wherein the plurality of impellers are joined to define an impeller assembly.

Device 29: The dry powder inhalation device according to device 21, wherein at least two of the plurality of impellers rotate about respective axes in a common rotational direction.

Device 30: The dry powder inhalation device according to device 21, wherein at least two of the plurality of impellers rotate about their respective axes in opposite rotational directions.

Device 31: The dry powder inhalation device according to device 21, wherein at least two of the plurality of impellers have different respective diameters.

Device 32: The dry powder inhalation device according to device 21, wherein at least two of the plurality of impellers have different respective heights.

Device 33: The dry powder inhalation device according to device 21, wherein at least one of the plurality of impellers is configured to achieve different airflow properties within the internal volume from at least one other of the plurality of impellers.

Device 34: The dry powder inhalation device according to device 21, wherein the plurality of impellers are configured to aerosolize the dry powder.

Device 35: The dry powder inhalation device according to device 21, wherein the one or more sidewalls surrounding the interior volume comprise one or more orifices therethrough, wherein the one or more orifices allow airflow through the one or more sidewalls surrounding the interior volume into the interior volume of the inhaler body.

Device 36: The dry powder inhalation device according to device 35, wherein at least one impeller of the assembly is positioned within the interior volume at a level that is between one or more of the orifices and the first end of the inhaler body.

Device 37: The dry powder inhalation device according to device 20, wherein the puncturing device is positioned within the interior volume at a level that is above a top side of an impeller and below the bottom side of the dry powder container.

Method 38: A method for delivering a dry powder into a lung of a subject comprising:

puncturing one or more walls of the dry powder container in the dry powder inhalation device of device 1 to provide one or more openings on the one or more walls of the dry powder container, and the subject inhaling the dry powder released from the dry powder container through the one or more openings.

Method 39: A method for delivering a dry powder into a lung of a subject comprising:

puncturing a plurality of walls of the dry powder container in the dry powder inhalation device of device 20, and the subject inhaling the dry powder released from the dry powder container through the one or more openings.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

It is to be understood that, while the subject technology has been described in conjunction with the detailed description, thereof, the foregoing description is intended to illustrate and not limit the scope of the subject technology. Thus, while there have been shown, described, and pointed out fundamental novel features of the invention as applied to several embodiments, it will be understood that various omissions, substitutions, and changes in the form and details of the devices illustrated, and in their operation, may be made by those skilled in the art without departing from the spirit and scope of the invention. Substitutions of elements from one described embodiment to another are also fully intended and contemplated. It is also to be understood that the drawings are not necessarily drawn to scale, but that they are merely conceptual in nature. The invention is defined solely with regard to the claims appended hereto, and equivalents of the recitations therein.

What is claimed is:

1. A dry powder inhalation device comprising: an inhaler body, the inhaler body comprising one or more sidewalls extending between an open first end and an open second end and surrounding an interior volume, at least a portion of the inhaler body being sized and shaped to receive an assembly of components within the interior volume; and the assembly of components, wherein the components are arranged in series within the interior volume and include: a dry powder container that contains a measured amount of dry powder, wherein one or more walls of the dry powder container are configured to be selectively opened thereby allowing the dry powder to be released from the container into the internal volume of the inhaler body, and a plurality of impellers positioned within the internal volume, wherein each of the plurality of impellers has a top side and an opposing bottom side and includes a series of blades defining openings therebetween and is configured to rotate about a respective central axis, and wherein the plurality of impellers are configured to direct air and the released dry powder toward the first end and wherein at least two of the plurality of impellers are configured to rotate about their respective axes in opposite rotational directions.

2. The dry powder inhalation device of claim 1, further comprising:

one or more puncturing devices configured to selectively open the one or more walls of the dry powder container.

3. The dry powder inhalation device of claim 2, wherein the one or more puncturing devices are positioned within the interior volume at a level that is above a top side of an impeller and below the bottom side of the dry powder container.

4. The dry powder inhalation device of claim 1, wherein the plurality of impellers are configured to rotate upon application of negative pressure to the first end of the inhaler body by a user inhaling air through the inhaler body from the first end.

5. The dry powder inhalation device of claim 4, wherein the rotation about the respective central axis of one of the plurality of impellers directs the air and the dry powder from above the top side of the impeller axially through the openings and through the internal volume of the inhaler body toward the first end.

6. The dry powder inhalation device of claim 5, wherein the plurality of impellers include a respective central axis pin and are supported within the internal volume by one or more mounts that are configured to receive an end of the respective central axis pin.

7. The dry powder inhalation device of claim 1, wherein one or more of the plurality of impellers are positioned within the interior volume at a level that is below the dry powder container and are configured to draw air and dry powder from the dry powder container through openings provided on a bottom side of the dry powder container.

8. The dry powder inhalation device of claim 1, wherein one or more of the plurality of impellers are positioned within the interior volume at a level that is above the dry powder container and are configured to direct air into the dry powder container through openings provided on at least a top side of the dry powder container.

9. The dry powder inhalation device of claim 1, wherein:
one or more of the plurality of impellers are positioned within the interior volume at a level that is below the dry powder container and are configured to draw air and dry powder from the dry powder container through openings provided on a bottom side of the dry powder container; and
one or more of the plurality of impellers are positioned within the interior volume at a level that is above the dry powder container and are configured to direct air into the dry powder container through openings provided on at least a top side of the dry powder container.

10. The dry powder inhalation device of claim 1, wherein the plurality of impellers are joined to define an impeller assembly.

11. The dry powder inhalation device of claim 1, wherein at least two of the plurality of impellers have different respective diameters.

12. The dry powder inhalation device of claim 1, wherein at least two of the plurality of impellers have different respective heights.

13. The dry powder inhalation device of claim 1, wherein at least one of the plurality of impellers is configured to achieve different airflow properties within the internal volume from at least one other of the plurality of impellers.

14. The dry powder inhalation device of claim 1, wherein the plurality of impellers are configured to aerosolize the dry powder.

15. The dry powder inhalation device of claim 1, wherein the one or more sidewalls surrounding the interior volume comprise one or more orifices therethrough, wherein the one or more orifices allow airflow through the one or more sidewalls surrounding the interior volume into the interior volume of the inhaler body.

16. The dry powder inhalation device of claim 15, wherein at least one impeller of the assembly is positioned within the interior volume at a level that is between one or more of the orifices and the first end of the inhaler body.

17. The dry powder inhalation device of claim 1, wherein one or more of the components defining the assembly of components are positioned within the interior volume independent of the remaining components.

* * * * *